United States Patent
Brush et al.

(10) Patent No.: US 7,951,959 B2
(45) Date of Patent: May 31, 2011

(54) HYDROPHILIC LABELS FOR BIOMOLECULES

(75) Inventors: Charles K. Brush, Middleton, WI (US); Kaizhang He, Whitefish Bay, WI (US); Peter T. Czerney, Weimar (DE); Matthias Wenzel, Jena (DE)

(73) Assignee: Thermo Fisher Scientific (Milwaukee) LLC, Milwaukee, WI (US)

( * ) Notice: Subject to any disclaimer, the term of this patent is extended or adjusted under 35 U.S.C. 154(b) by 0 days.

(21) Appl. No.: 12/560,957

(22) Filed: Sep. 16, 2009

(65) Prior Publication Data

US 2010/0069258 A1    Mar. 18, 2010

Related U.S. Application Data

(60) Provisional application No. 61/097,708, filed on Sep. 17, 2008.

(51) Int. Cl.
- *C07D 209/02* (2006.01)
- *C40B 30/04* (2006.01)
- *C07K 14/00* (2006.01)
- *C07K 16/00* (2006.01)
- *C07K 14/42* (2006.01)
- *C07K 14/575* (2006.01)
- *C07H 19/20* (2006.01)
- *C07H 21/00* (2006.01)
- *C12N 9/96* (2006.01)
- *G01N 21/00* (2006.01)
- *G01N 27/26* (2006.01)
- *C12Q 1/00* (2006.01)
- *C12Q 1/02* (2006.01)

(52) U.S. Cl. ........ 548/455; 548/469; 548/490; 548/492; 548/494; 506/9; 530/402; 530/391.1; 530/370; 530/399; 536/26.26; 536/22.1; 435/188; 435/4; 435/29; 435/6; 204/450

(58) Field of Classification Search .................. 548/455, 548/469, 490, 492, 494
See application file for complete search history.

(56) References Cited

U.S. PATENT DOCUMENTS

| | | | |
|---|---|---|---|
| 5,268,486 A | 12/1993 | Waggoner et al. | |
| 5,627,027 A | 5/1997 | Waggoner | |
| 5,846,737 A | 12/1998 | Kang | |
| 6,083,485 A | 7/2000 | Licha et al. | |
| 6,641,093 B2 | 11/2003 | Coudrais | |
| 6,974,873 B2 | 12/2005 | Leung et al. | |
| 6,977,305 B2* | 12/2005 | Leung et al. | 548/450 |
| 2007/0128659 A1* | 6/2007 | Czerney et al. | 435/7.1 |
| 2007/0178512 A1 | 8/2007 | Leung et al. | |

FOREIGN PATENT DOCUMENTS

| | | |
|---|---|---|
| DE | 4445065 | 6/1996 |
| DE | 19717904 A1 | 10/1998 |
| DE | 19926460 A1 | 12/1999 |
| DE | 10046215 A1 | 4/2002 |
| DE | 10046215 B4 | 4/2002 |
| EP | 1181940 A2 | 2/2002 |
| EP | 1181940 B1 | 2/2002 |
| EP | 1 322 710 B1 | 7/2003 |
| JP | 05-313304 | 11/1993 |
| WO | WO 02/26891 A1 | 4/2002 |
| WO | WO2005/044923 | 5/2005 |
| WO | WO 2005/103162 A1 | 11/2005 |

OTHER PUBLICATIONS

Search Report issued by the German Patent Office regarding APP #10 2006 029 454.8 issued Oct. 10, 2006 (with English language summary).

Search Report issued by the German Patent Office regarding APP #10 2006 057 345.5 issued May 21, 2007 (with English language summary).

* cited by examiner

*Primary Examiner* — Yong Chu
(74) *Attorney, Agent, or Firm* — Thompson Hine LLP

(57) ABSTRACT

Compounds, compositions, and methods for optical, including fluorescence optical, determinations useful in labeling biomolecules such as protein and deoxyribonucleic acid for their detection and quantitation. The compounds are diastereomeric cyanines with high hydrophilicity and other desirable properties.

14 Claims, 2 Drawing Sheets

(2 of 2 Drawing Sheet(s) Filed in Color)

HYDROPHILIC LABELS FOR BIOMOLECULES

This application claims priority from U.S. patent application Ser. No. 61/097,708, filed Sep. 17, 2008, incorporated by reference herein in its entirety.

Compounds and compositions, and methods using the compounds and compositions as labels for detecting and quantitating biomolecules such as proteins and nucleic acids in a sample.

Compounds that indicate the reaction of biomolecules (e.g., antigens, antibodies, deoxyribonucleotide (DNA)-segments) with a corresponding complimentary species to form a conjugate, are useful to measure enzyme kinetics, receptor-ligand interactions, nucleic acid hybridization kinetics in vitro, nucleic acid hybridization kinetics in vivo, etc. Such compounds are termed labels or dyes and may be used, for example, for pharmacological characterization of receptors and drugs.

Xanthylium salts (e.g., U.S. Pat. No. 5,846,737) and cyanines (e.g., U.S. Pat. No. 5,627,027) have been used as labels, but they tended to aggregate and to form dimers, especially in aqueous solution, due to planarity of their π-system. Labels that are insufficiently hydrophilic undergo non-specific interactions with various surfaces. This causes problems in purifying the corresponding conjugate and lead to an unsatisfactory signal to noise ratio.

In an attempt to reduce the disadvantages of cyanine labels, additional substituents that increase hydrophilicity have been introduced to labels. For example, additional sulfonic acid substituents have been introduced into the cyanine chromophore. Licha U.S. Pat. No. 6,083,485 and Molecular Probes U.S. patent application Ser. Nos. 09/968,401 and 09/989,853 disclose cyanines in which one of the common methyl groups in the 3-position of the terminal indole heterocycle is substituted by an ω-carboxyalkyl function, and in which the previously present (e.g. in Cy3 or Cy5) N-alkyl or N-ω-carboxyalkyl functions are replaced by N-ω-alkyl sulfonic acid functions. WO 05/044923 discloses cyanines in which the common methyl substituent in the 3-position of the terminal indole heterocycle is substituted by a N-ω-alkyl sulfonic acid function. U.S. Published Patent Application No. 2007/0128659 published Jun. 7, 2007, discloses trisulfonated-diastereomeric cyanines having a N-ω-alkyl sulfonic acid function that are useful in labeling biomolecules. Cyanines with more than two sulfonic acid functions disclosed in these documents exhibited higher solubility and a corresponding lower tendency to form dimers, in comparison to cyanines (Cy3, Cy5) described in U.S. Pat. No. 5,627,027.

Further improvements are desirable.

Compounds that are cyanine dyes having specific sulfonated groups are disclosed. More specifically, disulfonated diastereomeric compounds, also referred to as dyes, compositions of these dyes, and methods of using these dyes to label biomolecules are disclosed.

The compounds may be used in a manner similar to that disclosed in U.S. Published Patent Application No. 2007/0128659.

Diastereomeric compounds, and dye compositions and methods using the compounds, of general formula I or formula II, where formula I includes the enantiomers Ia1, Ia2, Ia3 and Ia4, and formula II includes the enantiomers IIa1, IIa2, IIa3 and IIa4, are disclosed.

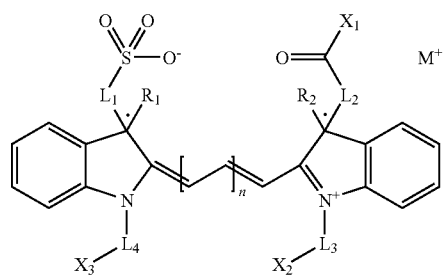

I

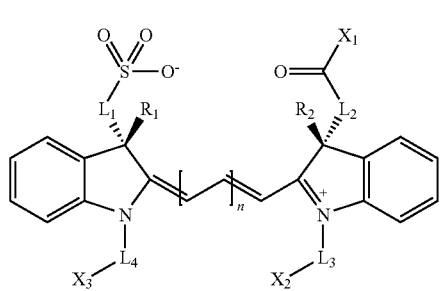

Ia1

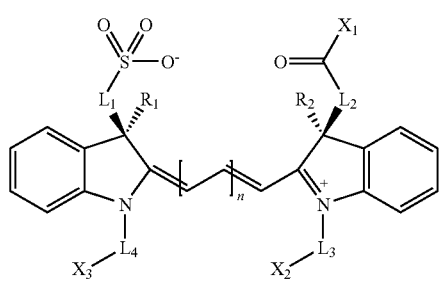

Ia2

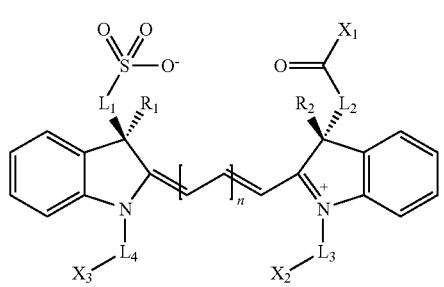

Ia3

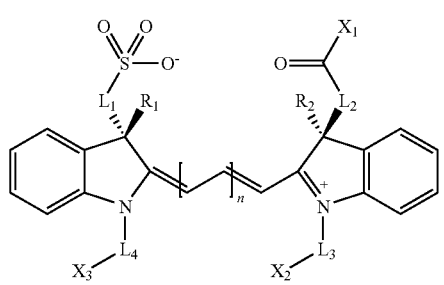

Ia4

-continued

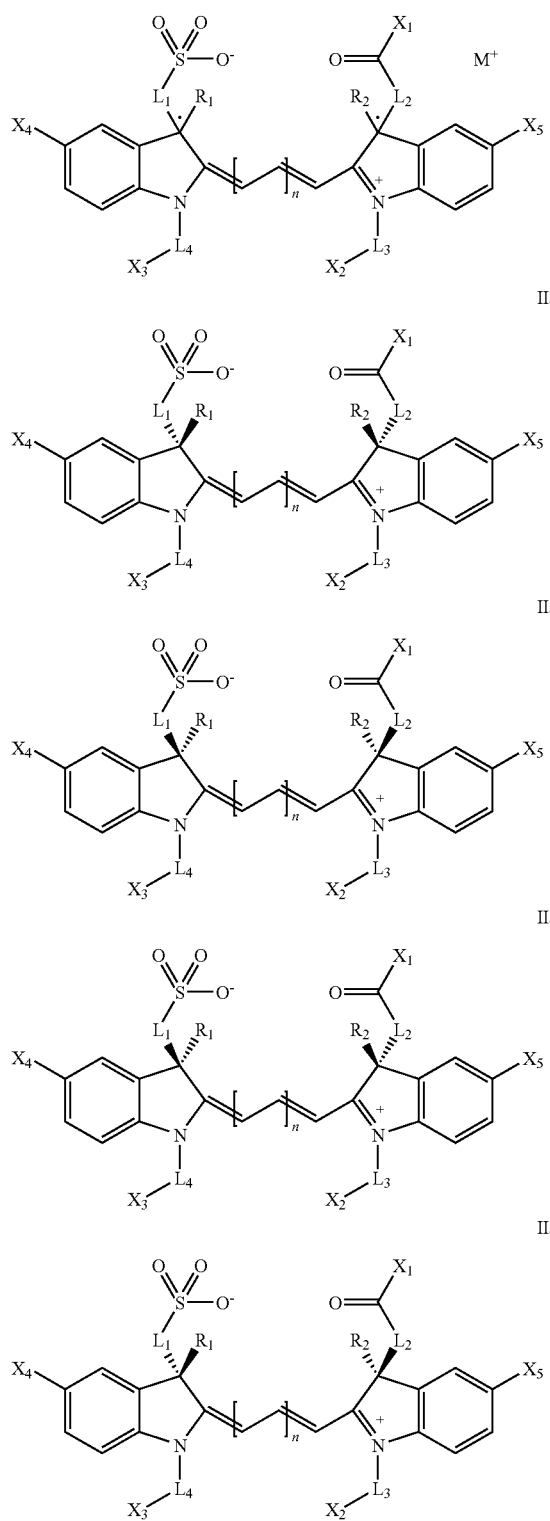

wherein n is an integer from 1-3;

each of $R_1$ and $R_2$ is the same or different and is independently selected from the group consisting of an aliphatic and heteroaliphatic group containing, e.g., 1-6 carbon atoms;

each of $L_1$ to $L_4$ is the same or different and is independently selected from the group consisting of a divalent linear (—$(CH_2)_o$—, o=1-15), branched, or cyclic alkylene group that can include at least one linkage selected from the group consisting of —O—, —N—, and —S—;

$X_1$ is selected from the group consisting of —OH, —SH, —$NH_2$, —NH—$NH_2$, —F, —Cl, —Br, —I, —NHS (hydroxysuccinimidyl/sulfosuccinimidyl), —O-STP (4-sulfo-2,3,5,6-tetrafluorophenoxy), —O-TFP (2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2H$, —NR-L-$CO_2$—NHS, —NR-L-$CO_2$-STP, —NR-L-$CO_2$-TFP, —NR-L-CO-benzotriazole, —NR-L-CHO, —NR-L-maleimide, and —NR-L-NH—CO—$CH_2$—I;

R is —H or is equal to $R_1$ and $R_2$,

L is equal to $L_1$ to $L_4$;

each of $X_2$ and $X_3$ is the same or different and is independently selected from the group consisting of hydrogen, alkyl-, tert-alkyl-, aryl-, carboxyaryl-, dicarboxyaryl-, heteroaryl-, cycloalkyl-, heterocycloalkyl-, alkyloxy-, alkylmercapto-, aryloxy, arylmercapto, hydroxy-, amino-, nitro-, and cyano-residues, or is a solubilizing or ionizable substituent selected from the group consisting of —$SO_3^-$, —$PO_3^{2-}$, —$CO_2^-$, tert-ammonium, cyclodextrine, sugar, and combinations thereof; with the proviso that in Formula I, one of $X_2$ or $X_3$ is —$SO_3^-$;

In formula II, one of $X_4$ or $X_5$ is hydrogen and the other is —$SO_3^-$.

In formulas I and II, $M^+$ is one or more $Na^+$, $K^+$, $Ca^{2+}$, ammonia, or other cation(s) needed to provide a neutral charge, and n is an integer from 1-3;

In one embodiment, the compounds are conjugated to a deoxyribonucleotide triphosphate (dNTP) or ribonucleotide triphosphate (NTP). In this embodiment, the compounds are enzymatically incorporated into the nucleic acid at an enhanced rate, and thus provide enhanced performance in enzymatic incorporation reactions. In one embodiment, the compounds are conjugated to deoxyribouridine triphosphate (dUTP). In one embodiment, the compounds are conjugated to deoxyribocytidine triphosphate (dCTP). In one embodiment, the compounds are conjugated to 7-deaza-deoxyguanosine triphosphate (7-deaza-dGTP). In one embodiment, the compounds are conjugated to 7-deaza-deoxyadenosine triphosphate (7-deaza-dATP) In one embodiment, the compounds are conjugated to 7-deaza-deoxyinosine triphosphate (7-deaza-dITP). In one embodiment, the compounds are conjugated to 7-deaza -2-aminopurine-triphosphate. In one embodiment, the compounds are conjugated to 7-deaza-8-aza-deoxyadenosine triphosphate (7-deaza-8-aza-dATP). In one embodiment, the compounds are conjugated to 7-deaza-8-aza-deoxyguanosine triphosphate (7-deaza-8-aza-dGTP). In one embodiment, the compounds are conjugated to $N^4$-deoxycytosine triphosphate ($N^4$-dCTP).

In one embodiment, the compounds incorporated into the nucleic acid are used to extend primers. In one embodiment, the compounds incorporated into the nucleic acid are used in labeling of PCR amplicons with Taq polymerase. In one embodiment, the compounds incorporated into the nucleic acid are used in labeling of PCR amplicons with Tth™ DNA polymerase. In one embodiment, the compounds incorporated into the nucleic acid are used in labeling of PCR amplicons with VENT™ DNA polymerase. In one embodiment, the compounds incorporated into the nucleic acid are used in labeling of PCR amplicons with Klenow polymerase. The dye-dUTP conjugates demonstrated significantly higher labeling of products, in comparison to other commercially available compounds used as dyes, such as the pentamethine dyes Cy5, DY 649, and Alexa 647 that, when conjugated to dUTP or dCTP, are not as readily incorporated into nucleic acids by DNA polymerases. Applications using dyes, such as labeled cDNA synthesis, labeling by PCR, primer extension, and single base extension, would benefit from a pentamethine dye that is incorporated at a higher rate, thereby producing more signal and greater sensitivity in an assay.

The following description and examples further illustrate additional embodiments.

The patent or application file contains at least one drawing executed in color. Copies of this patent or patent application publication with color drawing(s) will be provided by the Office upon request and payment of the necessary fee.

Figure 1:
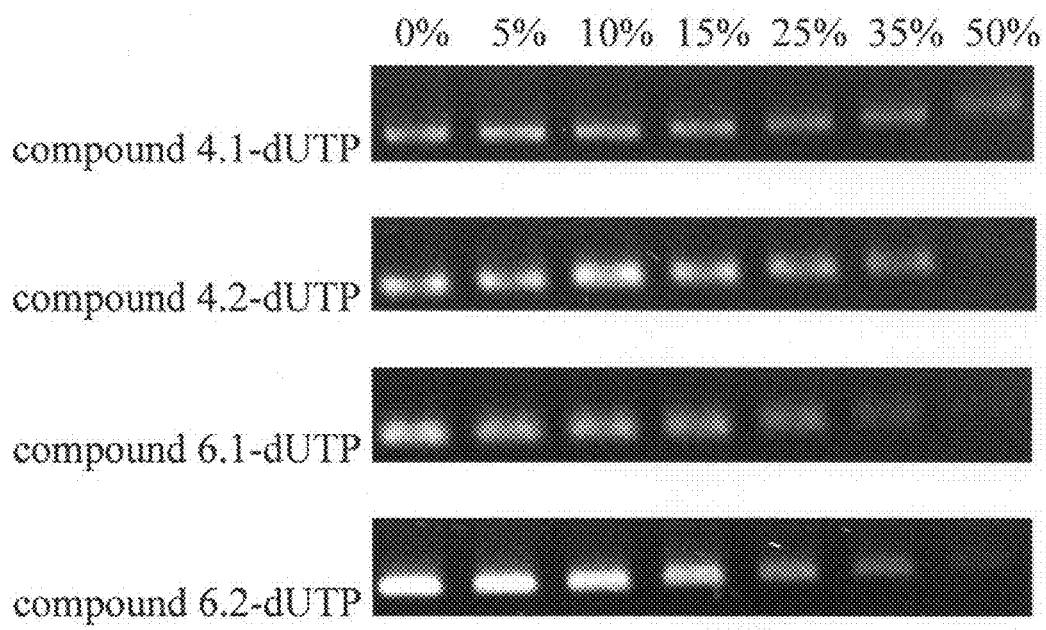
FIG. 1 shows ethidium bromide-stained gels of PCR products amplified in the presence of a deoxynucleotide triphosphate labeled with a disclosed compound.

Diastereomeric cyanine compounds are disclosed that are useful as labels in optical, especially fluorescence optical, determination and detection methods. The compounds, also referred to herein as dyes and/or labels, have high hydrophilicity, high molar absorbance, high photo-stability, and high storage stability. These compounds can be excited by monochromatic (e.g., lasers, laser diodes) or polychromatic (e.g., white light sources) light in the ultraviolet (UV), visible, and near infrared (NIR) spectral region to generate emission of fluorescence light.

In one embodiment of the compounds of formula I:
each of $R_1$ and $R_2$ is independently a C1-C3 alkyl group; in one embodiment, each of $R^1$ and $R_2$ is methyl;
each of $L_1$ and $L_2$ is a C3-C5 alkylene bridge; in one embodiment each of $L_1$ and $L_2$ is propyl;
$X_1$ is —OH or —NHS;
each of $L_3$ and $L_4$ is a C1-C3 alkylene bridge; in one embodiment, $L_3$ is propyl and $L_4$ is methylene (compound formula Ia); in one embodiment, $L_3$ is methylene and $L_4$ is propyl (compound formula 1b);
one of $X_2$ or $X_3$ is C1-C3 alkyl and the other of $X_2$ or $X_3$ is —$SO_3^-$; in one embodiment, one of $X_2$ or $X_3$ is methyl and the other of $X_2$ and $X_3$ is —$SO_3$ (compound formulas 1a and 1b)$^-$; and
n is 2.

In one embodiment of the compounds of formula II:
each of $R_1$ and $R_2$ is independently a C1-C3 alkyl group; in one embodiment, each of $R^1$ and $R_2$ is methyl (compound formulas IIa and IIb);
each of $L_1$ and $L_2$ is a C3-C5 alkylene bridge; in one embodiment each of $L_1$ and $L_2$ is propyl (compound formulas IIa and IIb);
$X_1$ is —OH or —NHS;
each of $L_3$ and $L_4$ is a C1-C3 alkylene bridge; in one embodiment, each of $L_3$ and $L_4$ is methylene (compound formulas IIa and IIb);
each of $X_2$ and $X_3$ is C1-C3 alkyl; in one embodiment, each of $X_2$ and $X_3$ is methyl (compound formulas IIa and IIb);
one of $X_4$ or $X_5$ is hydrogen and the other is —$SO_3^-$; and
n is 2.

Representative disulfonated compounds (single diastereomer shown) are

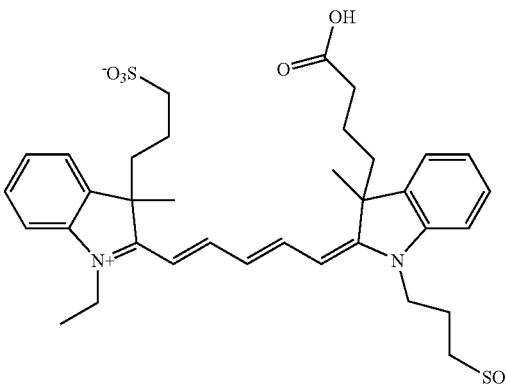

Compound formula Ia

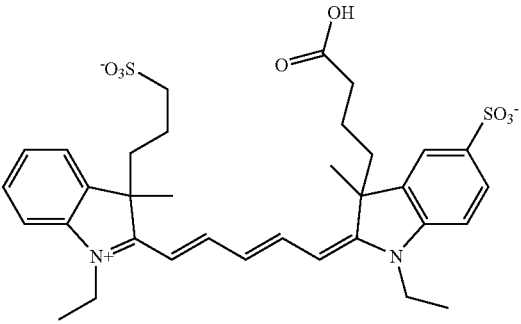

Compound formula IIa

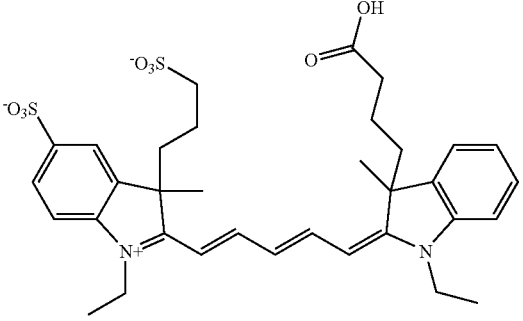

Compound formula IIb

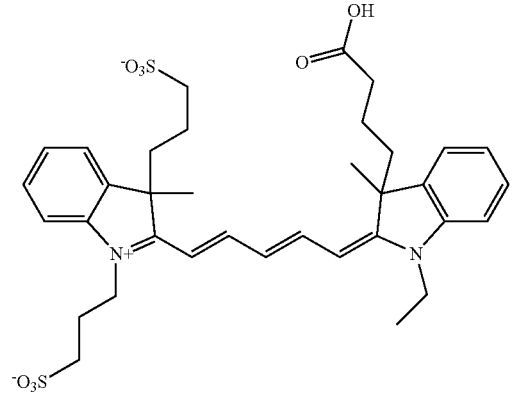

Compound formula Ib

One example of a dUTP conjugated to the diastereoisomeric Compound formula IIb is shown below:

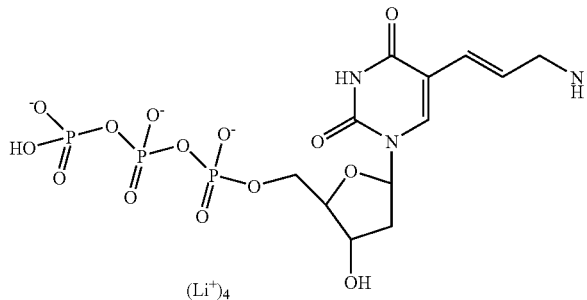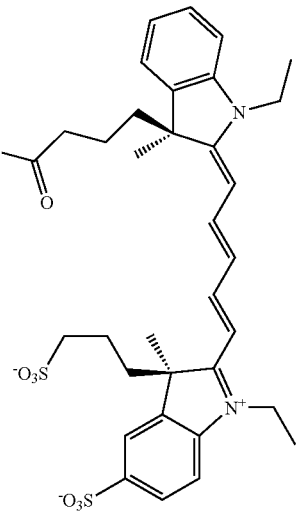

The present application discloses use of cyanines in which one terminal heterocycle has, in 3-position, a solubilizing or ionizing group (e.g. ω-alkyl sulfonic acid function) and in which the other terminal heterocycle has a function for the coupling to biomolecules (e.g. a ω-carboxyalkyl function). These cyanines exhibit a chiral C-atom in each 3-position through derivatizing both terminal indole heterocycles in 3-position, once with a ω-alkyl sulfonic acid function and once with a ω-carboxyalkyl function, resulting in a mixture of diastereomers.

In one embodiment, the number of sulfonate groups, and their distribution on the cyanine compound, influences the extent of the compound's incorporation into nucleic acids. This is demonstrated in the following table:

In one embodiment, the compounds are covalently conjugated to biomolecules using the ω-carboxyalkyl function positioned at the 3-position of the indole ring. In one embodiment, this function can be activated by protein chemistry methods known to a person of ordinary skill in the art, e.g., formation of N-hydroxysuccinimidyl ester (NHS-ester), acid fluoride, tetrafluorophenyl ester (TFP-ester), or STP-ester, such that it reacts with the amino function of the biomolecule with the formation of an acid amide. The coupling reaction may be performed in organic or aqueous solutions between pH 5 and pH 12. The compound need not be dissolved in an organic solvent, such as dimethyl formamide (DMF) or dimethyl sulfoxide (DMSO) prior to adding the sample to be evaluated. In one embodiment, the coupling reaction may be performed in a 100% aqueous solution in the absence of an

| Compound | # $SO_3^-$ groups | Diastereomer | Separated | Substitution sites | Relative Fluorescent Units (RFU) | Standard Deviation |
|---|---|---|---|---|---|---|
| Alexa 647 | 4 | N | N/A | ? | 4.1 | 0.4 |
| Cy5 | 2 | N | N/A | 5, 5' | 25.3 | 4.1 |
| DY 649 | 4 | Y | N | N, 5, 5', 3' | 0.6 | 0.4 |
| compound IIa | 2 | Y | Y | 3', 5 | 18.1 | 0.6 |
| compound 6.1 | 2 | Y | Y | 3, 5 | 36.6 | 1.1 |
| compound 6.2 | 2 | Y | Y | 3, 5 | 40.6 | 0.7 |

The disclosed compounds can be used as chromophores and/or fluorophores. They can be used for optical labelling and, therefore, for the qualitative and/or quantitative detection of proteins, nucleic acids, oligomers, DNA, RNA, biological cells, lipids, mono-, oligo- and polysaccharides, ligands, receptors, polymers, drugs, polymeric beads, etc. They react with biomolecules such as proteins (e.g., antigens, antibodies, etc.), DNA and/or RNA segments, etc. Thus, among other embodiments, measurements of enzyme kinetics, receptor-ligand interactions, and nucleic acid hybridization kinetics in vitro as well as in vivo are enabled. The compounds are of interest for the pharmacological characterization of receptors and drugs. Applications include, but are not limited to, uses in medicine, pharmacy, biological sciences, materials sciences, environmental control, detection of organic and inorganic micro samples occurring in nature, etc.

organic solvent. In one embodiment, performing the coupling reaction in an aqueous solution preserves the activity of the biomolecule. In one embodiment, the coupling reaction may be performed at room temperature (about 20° C. to about 22° C.).

The resulting compound and biomolecule conjugates exhibit fluorescent properties. They may be used in optical, including fluorescence optical, qualitative and quantitative determination methods. Examples of such methods include, but are not limited to, immunoassays, hybridization methods, chromatographic methods, electrophoretic methods, fluorescence resonance energy transfer (FRET) systems, high throughput screenings, analysis of receptor-ligand interactions on a microarray, etc.

Compounds of the general formulas I and/or II and any of the embodiments can be used as dyes for optical labeling of organic or inorganic biomolecules, also referred to as recognition units. Recognition units are molecules having specificity and/or affinity for a specific group of molecules. Examples of recognition units include, but are not limited to, antibodies that have affinity for antigens; enzymes that bind and/or react with a specific bond or bonds within a sequence of amino acids in a peptide or react with a substrate; cofactors such as metals that enhance or inhibit specific interactions; lectins that bind specific sugars or sugar sequences (e.g., oligosaccharides, polysaccharides, dextrans, etc.); biotin binding proteins such as avidin and streptavidin that bind biotin and biotinylated molecules; antibody binding proteins such as Protein A, Protein G, Protein A/G and Protein L, sequences of amino acids or metals that have affinity for each other (e.g., histidine sequences that bind nickel or copper, phosphate containing proteins that bind gallium, aluminium, etc.); specific sequences of nucleic acids such as DNA and/or RNA oligonucleotides that have affinity for proteins, specific sequences of amino acids that have affinity for DNA and/or RNA, haptens, carotenoids, hormones (e.g., neurohormone), neurotransmitters, growth factors, toxins, biological cells, lipids, receptor binding drugs or organic or inorganic polymeric carrier materials, fluorescent proteins such as phycobilliproteins (e.g., phycoethrin, allophycocyanin), etc. The recognition unit and compound can be covalently connected. The result is a conjugate for qualitative or quantitative determination of various biomaterials or other organic or inorganic materials using optical methods.

Compounds of the general formulas I and/or II, compositions containing the compounds with at least one biocompatible excipient, and systems derived from the compounds and composition, can be used in optical, including fluorescence optical, qualitative and quantitative determination methods to diagnose properties of cells (molecular imaging), in biosensors (point of care measurements), for investigation of the genome, and in miniaturizing technologies. Cytometry, cell sorting, fluorescence correlation spectroscopy (FCS), ultra high throughput screening (uHTS), multicolor fluorescence in situ hybridisation (mc-FISH), FRET-systems and microarrays (DNA- and protein chips) are some examples of fields of application.

A microarray is a grid-like arrangement of molecules immobilized on at least one surface. The microarray can be used to study, for example, receptor ligand interactions. A grid-like arrangement means more than two molecules different from each other that are located within an area and in different predefined regions with known position.

A receptor is a molecule that exhibits an affinity to a given ligand. Receptors can be naturally occurring or artificially made molecules. Receptors can be used in their pure form or bound to another specie. Receptors can be coupled covalently or noncovalently to a binding partner either directly or through a coupling mediator. Examples for receptors include but are not limited to agonists and antagonists for cell membrane receptors, toxins and other poisons, viral epitopes, hormone like opiates and steroids, hormone receptors, peptides, enzymes, enzyme substrates, drugs acting as cofactors, lectins, sugars, oligonucleotides, nucleic acids, oligosaccharides, cells, cell fragments, tissue fragments, proteins, antibodies, etc. A ligand is a molecule that is recognized by a certain receptor. Examples for ligands include but are not limited to agonists and antagonists for cell membrane receptors, toxins and other poisons, viral epitopes, hormones like opiates and steroids, hormone receptors, peptides, enzymes, enzyme substrates, drugs acting as cofactors, lectins, sugars, oligonucleotides, nucleic acids, oligosaccharides, proteins, antibodies, etc.

As further disclosed in Examples 1 and 2 below, in one embodiment, the compounds of formulas I and II were synthesized by condensing the two differently substituted acidic indole heterocycles and a C-1, C-3, or C-5 building block. Additional methods for synthesis may be used. One example involves condensing one of the acidic indole heterocycles in a first reaction step with the C-1, C-3, or C-5 building block, followed by isolating the 1:1 condensation product which is reacted subsequently with the second CH-acidic indole heterocycle through condensation to the cyanine. The sequence of use of the CH-acidic indole heterocycles is thereby irrelevant. Thus, a plurality of differently functionalized, strongly hydrophilic, diastereomeric compounds that differ in total charge and specifity/reactivity of the active groups used for their immobilization can be easily prepared.

The disclosed compounds may be modified with reactive groups that include, but are not limited to, iodoacetyl, maleimide, hydrazides, N-hydroxysuccinimides, sulfonyl chloride, phenylazides, and others as known to a person of ordinary skill in the art, may be used to label macromolecules (e.g., antibodies, streptavidin, etc) using methods known to a person of ordinary skill in the art. For example, streptavidin, reconstituted or dialyzed against sodium borate or sodium carbonate buffer, between pH 8.5 to pH 9.0, may be reacted with a 5-10 molar excess of N-hydroxysuccnimide activated cyanine dye that is sulfonated and free of hydrophobic groups. The reaction is carried out for one to two hours at room temperature (about 20° C. to about 22° C.) and then dialyzed against several changes of phosphate buffered saline (pH 7.2). The resulting dye-macromolecule conjugates may be used in applications such as in detection of specific proteins in immunoassays, sugars in glycoproteins with lectins, protein-protein interactions, oligonucleotides in nucleic acid, hybridization, and in Electrophoretic Mobility Shift Assays (EMSA).

In one embodiment, a kit comprises at least one of the compounds of formula I or II and instructions for labeling a biomolecule with the compound. In one embodiment, a kit comprises at least one biomolecule-bound compound of formula I or II and instructions for using the biomolecule-bound compound. For example, the kit may contain at least one of the compounds of formula I or II conjugated to at least one of a nucleoside triphosphate or a deoxynucleoside triphosphate. In one embodiment, the kit contains instructions for using the biomolecule-bound compound in a polymerase reaction.

The following examples further disclose the inventive compounds and methods.

EXAMPLE 1

Synthesis of Compounds of the General Formula I

Synthesis of 2-((1E,3E)-(3-[3-(3-Carboxy-propyl)-3-methyl-1-(3-sulfo-propyl)-1,3-dihydro-indol-(2E)-ylidene]-penta-1,3-dienyl}-1-ethyl-3-methyl-3-(3-sulfopropyl)-3H-indolium sodium salt 14

Compound formula Ia

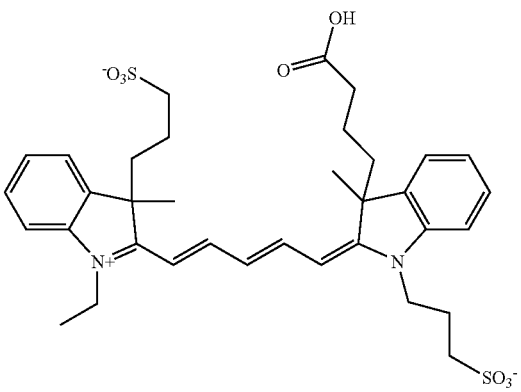

(14)

516 mg (1 mmol) 1-ethyl-3-methyl-2-((1E,3E)-4-phenylamino-buta-1,3-dienyl)-3-(3-sulfo-propyl)-3H-indolium sodium salt 12 and 387 mg (1 mmol) 3-(3-carboxypropyl)-2,3-dimethyl-1-(3-sulfopropyl)-3H-indolium iodide salt 13 were dissolved in a mixture of 10 ml acetic acid and 10 ml acetic anhydride.

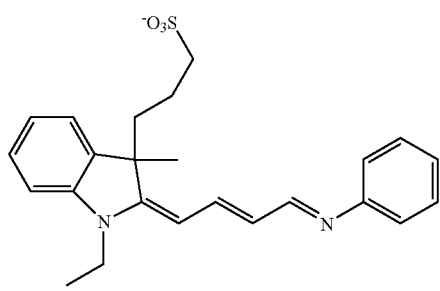

12

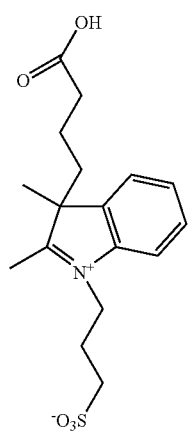

13

Subsequently, 5 ml pyridine was added. The solution was stirred under reflux for 15 minutes. After cooling to room temperature (about 20° C. to about 22° C.), 20 ml ether was added. The precipitate that was obtained was extracted by suction, washed with ether and dried.

The residue was purified by column chromatography: RP-18: methanol/water 1/1.

After cooling to room temperature (about 20° C. to about 22° C.), 20 ml ether was added. The precipitate that was obtained, which was a mixture of the diastereomers 14.1 and 14.2, was extracted by suction, washed with ether, and dried.

The residue was purified by column chromatography: RP-18: methanol/water 1/1.

The fractions containing the pure compounds 14.1 were combined and the solvent was removed by distillation. Similarly, the fractions containing pure compound 14.2 were combined and evaporated. The yield was about 15% per diastereomer.

Diastereomer 14.1:
UV-vis (ethanol): $\lambda_{max}$=650 nm
MS (ESI−): 683.2 [M]−
Diastereomer 14.2:
UV-vis (ethanol): $\lambda_{max}$=647 nm
MS (ESI−): 683.2 [M]−

Synthesis of 3-methyl-2-((E)-2-phenylamino-vinyl)-1,3-bis-(3-sulfo-propyl)-3H-indolium sodium salt 8

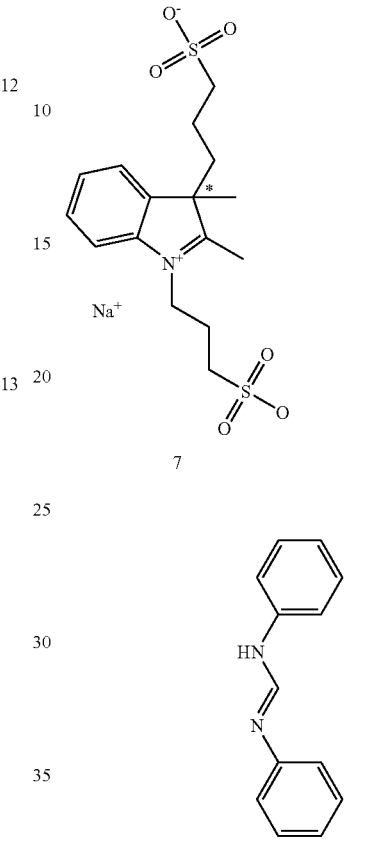

7

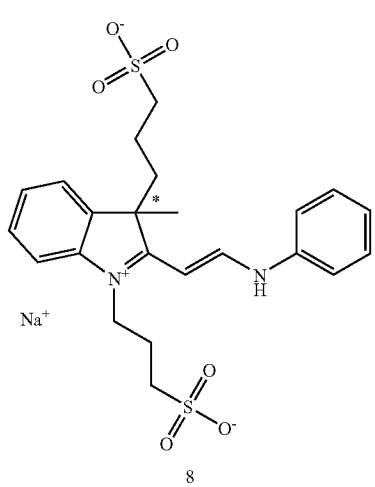

8

0.822 g (2 mmol) 2,3-dimethyl-1,3-bis-(3-sulfo-propyl)-3H-indolium sodium salt 7 and 0.49 g (2.5 mmol) N,N'-diphenyl-formamidine are dissolved in 20 ml methanol and stirred for about four hours under reflux. The solvent is removed in vacuum after cooling to room temperature. The residue is washed carefully with ethyl acetate. A dark yellow solid is obtained which is processed without further purification.

Synthesis of 2-((E)-3-[3-(carboxy-propyl)-1-ethyl-3-methyl-1,3-dihydro-indol-(2E)-ylidene]-propenyl)-3-methyl-1,3-bis-(3-sulfo-propyl)-3H-indolium sodium salt 9

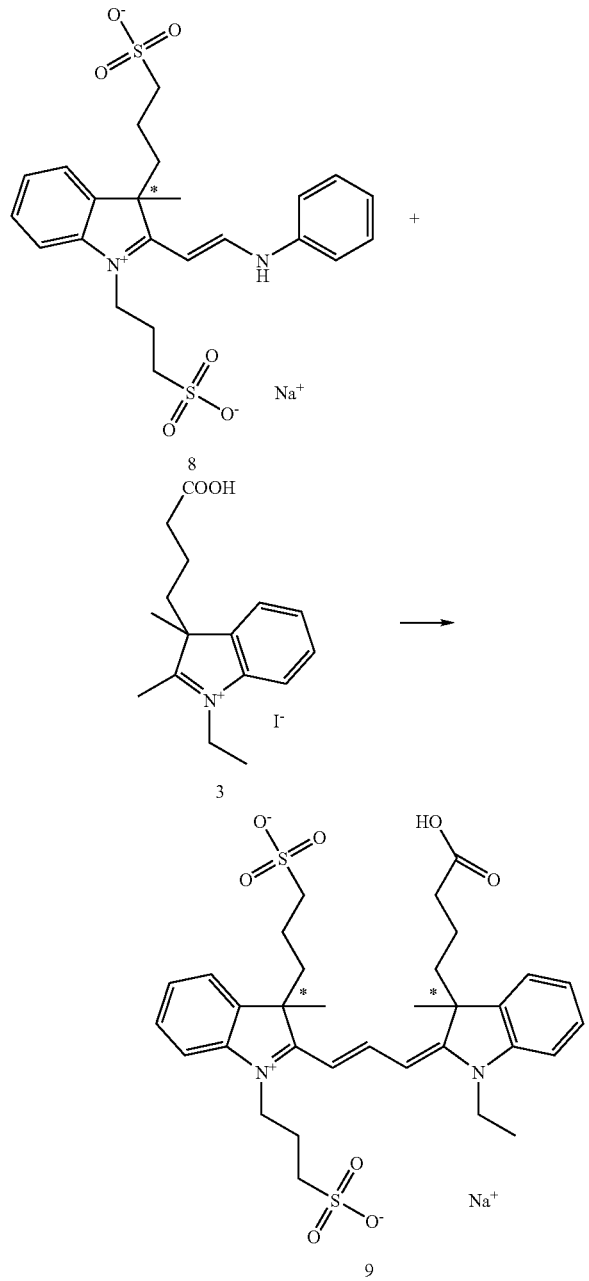

500 mg (1 mmol) 1-ethyl-3-methyl-2-((E)-2-phenylamino-vinyl)-5-sulfo-3-(3-sulfo-propyl)-3H-indolium sodium salt 8 and 387 mg (1 mmol) 3-(3-carboxypropyl)-2,3-dimethyl-1-ethyl-3H-indolium iodide salt 3 are dissolved in a mixture of 10 ml acetic acid and 10 ml acetic anhydride. Subsequently, 5 ml of pyridine is added. The solution is stirred under reflux for 15 minutes.

After cooling to room temperature, the solvent is removed. The obtained residue, which is a mixture of the diastereomers 9.1 and 9.2, is washed with ether and dried.

The residue is purified by column chromatography: RP-18: methanol/water 1/1.

The fractions containing the pure compounds 9.1 and 9.2 are combined and the solvent is removed by distillation. The yield is about 10% per diastereomer.

Diastereomer 9.1:
UV-vis (ethanol): $\lambda_{max}$=548 nm
MS (ESI–): 657.2 [M]⁻

Disasteromer 9.2:
UV-vis (ethanol): $\lambda_{max}$=546 nm
MS (ESI–): 657.1 [M]⁻

Synthesis of 3-methyl-2-((1E,3E)-4-phenylamino-buta-1,3-dienyl)-1,3-bis-(3-sulfo-propyl)-3H-indolium sodium salt 10

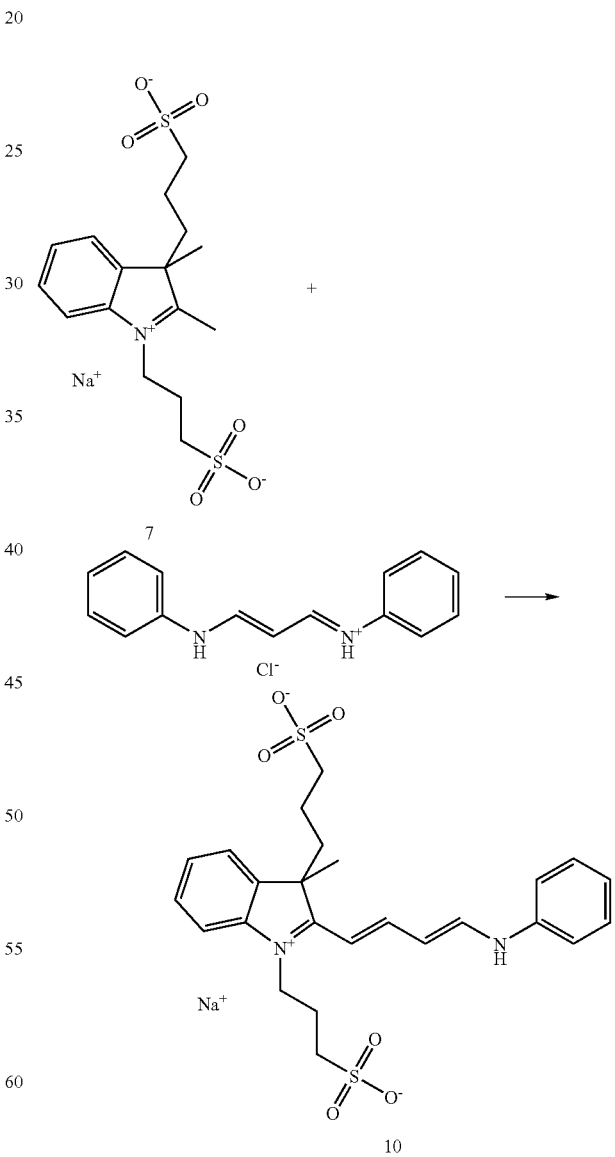

0.822 g (2 mmol) 2,3-dimethyl-1,3-bis-(3-sulfo-propyl)-3H-indolium sodium salt 7 and 0.65 g (2.5 mmol) malonaldehyde-bisphenylimine-hydrochloride are dissolved in a mixture of 10 ml acetic acid and 20 ml acetic anhydride and stirred at 120° C. for four hours. The solvent is removed in vacuum after cooling to room temperature. The residue is washed carefully with ethyl acetate. A dark brown solid is obtained which is processed without further purification.

Synthesis of 2-((1E,3E)-5-[3-(carboxy-propyl)-1-ethyl-3-methyl-1,3-dihydro-indol-(2E)-ylidene]-penta-1,3-dienyl)-3-methyl-1,3-bis-(3-sulfo-propyl)-3H-indolium sodium salt 11

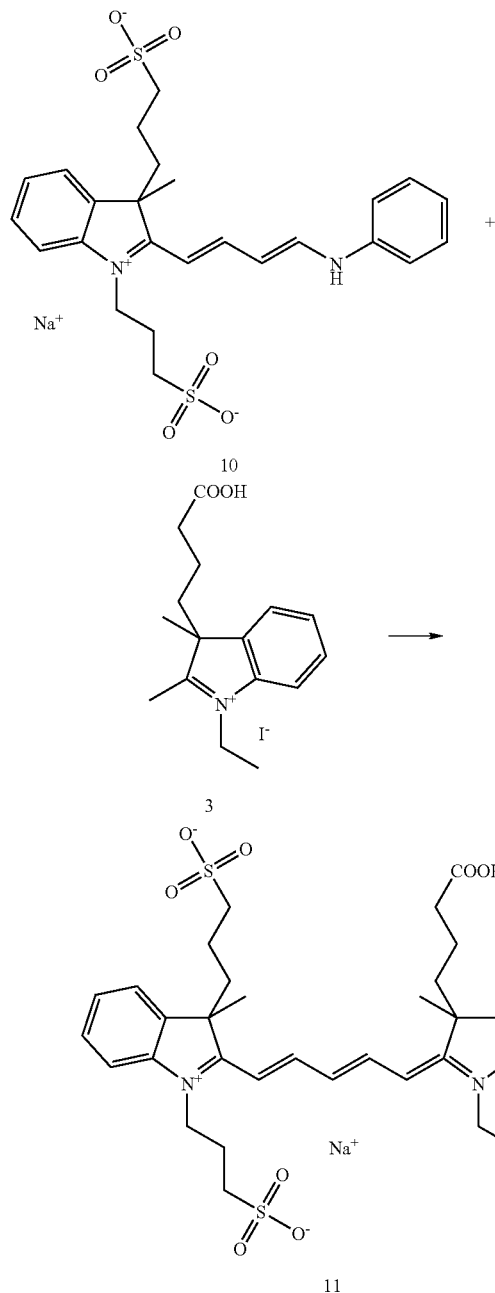

540 mg (1 mmol) 3-methyl-2-((1E,3E)-4-phenylamino-buta-1,3-dienyl)-1,3-bis-(3-sulfo-propyl)-3H-indolium sodium salt 10 and 387 mg (1 mmol) 3-(3-carboxypropyl)-2,3-dimethyl-1-ethyl-3H-indolium iodide salt 3 are dissolved in a mixture of 10 ml acetic acid and 10 ml acetic anhydride. Subsequently, 5 ml of pyridine is added. The solution is stirred under reflux for 15 minutes.

After cooling to room temperature, 20 ml ether is added. The obtained precipitate, which is a mixture of the diastereomers 11.1 and 11.2, is extracted by suction, washed with ether and dried.

The residue is purified by column chromatography: RP-18: methanol/water 1/1.

The fractions containing the pure compounds 11.1 and 11.2 are combined and the solvent is removed by distillation. The yield is about 15% per diastereomer.

Diastereomer 11.1:

UV-vis (ethanol): $\lambda_{max}$=648 nm

MS (ESI−): 683.2 [M]−

Disasteromer 11.2:

UV-vis (ethanol): $\lambda_{max}$=646 nm

MS (ESI−): 683.3 [M]−

EXAMPLE 2

Synthesis Compounds of the General Formula II

Synthesis of 1-ethyl-3-methyl-2-((E)-2-phenylamino-vinyl)-5-sulfo-3-(3-sulfo-propyl)-3H-indolium sodium salt 2

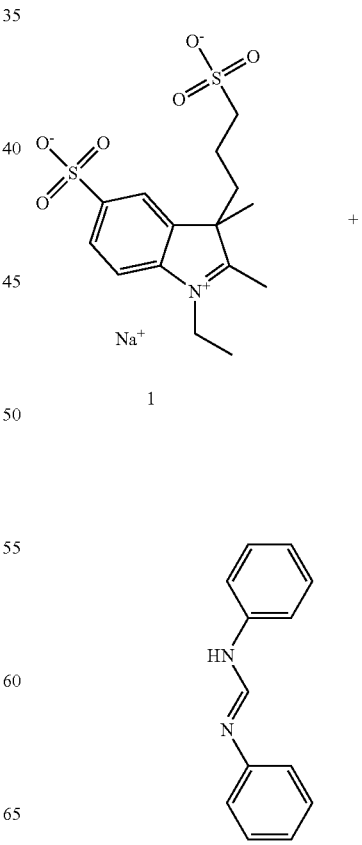

-continued

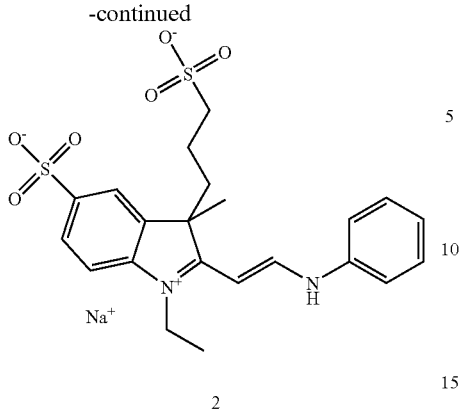

2

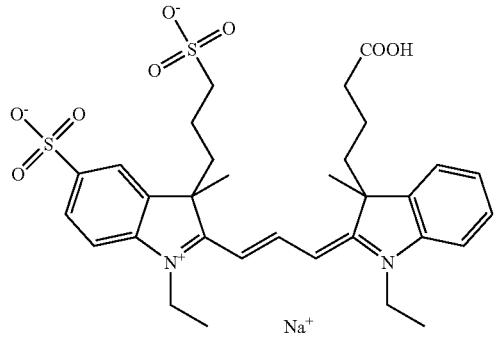

4

0.794 g (2 mmol) 3-(3-sulfopropyl)-2,3-dimethyl-5-sulfonato-1-ethyl-3H-indolium sodium salt 1 and 0.49 g (2.5 mmol) N,N'-diphenyl-formamidine were dissolved in 20 ml methanol and stirred for about four hours under reflux. The solvent was removed in vacuum after cooling to room temperature (about 20° C. to about 22° C.). The residue was washed carefully with ethylacetate. A dark yellow solid was obtained which was processed without further purification.

2-{(E)-3-[3-(3-Carboxy-propyl)-3-methyl-1-ethyl-1,3-dihydro-indol-(2E)-ylidene]-propenyl}-1-ethyl-3-methyl-5-sulfo-3-(3-sulfo-propyl)-3H-indolium sodium salt 4

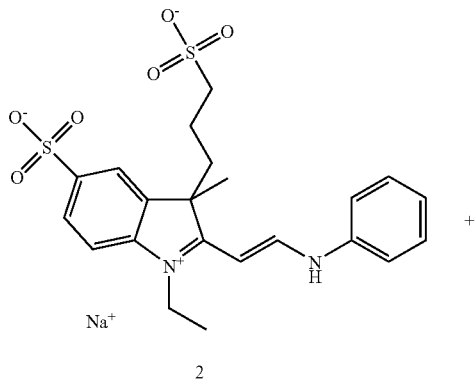

2

500 mg (1 mmol) 1-ethyl-3-methyl-2-((E)-2-phenylamino-vinyl)-5-sulfo-3-(3-sulfo-propyl)-3H-indolium sodium salt 2 and 387 mg (1 mmol) 3-(3-carboxypropyl)-2,3-dimethyl-1-ethyl-3H-indolium iodide 3 salt were dissolved in a mixture of 10 ml acetic acid and 10 ml acetic anhydride. Subsequently, 5 ml pyridine was added. The solution was stirred under reflux for 15 minutes. After cooling to room temperature (about 20° C. to about 22° C.), 20 ml ether was added. The precipitate that was obtained, which was a mixture of the diastereomers 4.1 and 4.2, was extracted by suction, washed with ether, and dried. The residue was purified by column chromatography: RP-18: methanol/water 1/1.

The fractions containing the pure compound 4.1 were combined and the solvent was removed by distillation. Similarly, the fractions containing pure compound 4.2 were combined and evaporated. The yield was about 15% per diastereomer.

Diastereomer 4.1:

UV-vis (ethanol): $\lambda_{max}$=556 nm

MS (ESI−): 740.1 [M]−

Diastereomer 4.2:

UV-vis (ethanol): $\lambda_{max}$=558 nm

MS (ESI−): 740.2 [M]−

Synthesis of 1-ethyl-3-methyl-2-((1E,3E)-4-phenylamino-buta-1,3-dienyl)-5-sulfo-3-(3-sulfo-propyl)-3H-indolium sodium salt 5

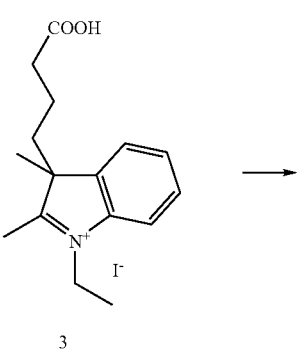

3

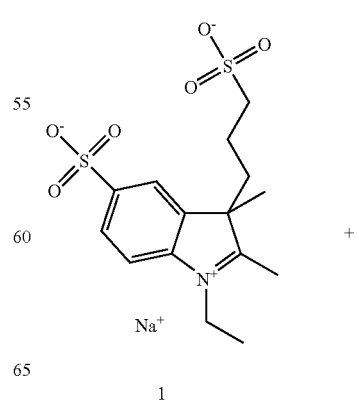

1

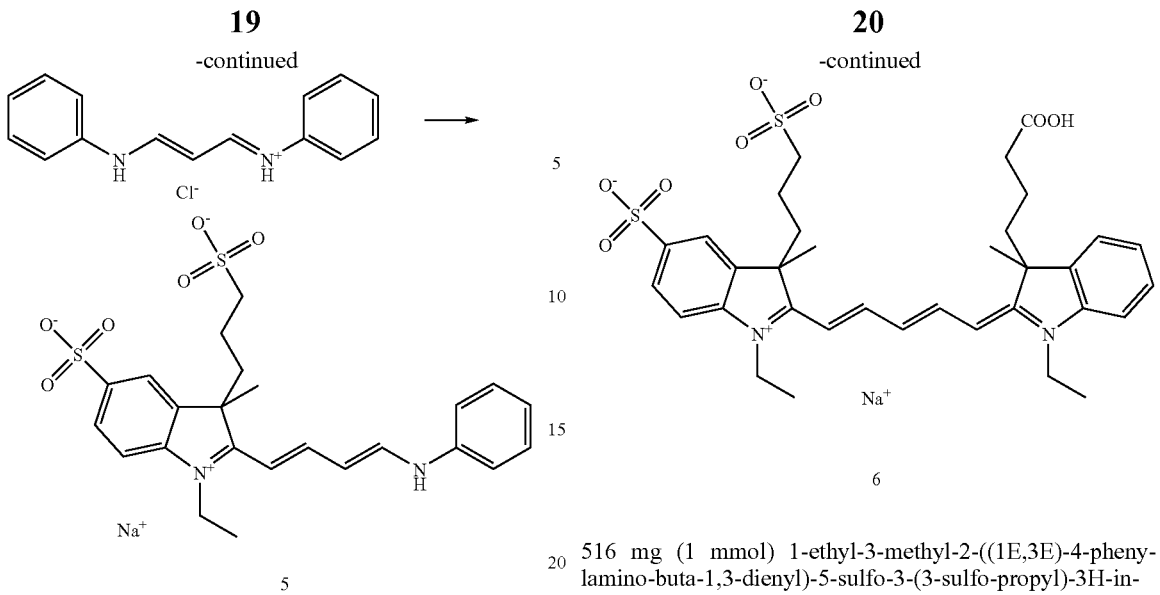

0.794 g (2 mmol) 3-(3-sulfopropyl)-2,3-dimethyl-5-sulfonato-1-ethyl-3H-indolium sodium salt 1 and 0.65 g (2.5 mmol) malonaldehyd-bisphenylimine-hydrochloride were dissolved in a mixture of 10 ml acetic acid and 10 ml acetic anhydride and stirred at 120° C. for four hours. The solvent was removed in vacuum after cooling to room temperature. The residue was washed carefully with ethylacetate. A dark brown solid was obtained that was processed without further purification.

Synthesis of 2-{(1E,3E)-5-[3-(3-carboxy-propyl)-3-methyl-1-ethyl-1,3-dihydro-indol-(2E)-ylidene]-penta-1,3-dienyl}-1-ethyl-3-methyl-5-sulfo-3-(3-sulfo-propyl)-3H-indolium sodium salt 6

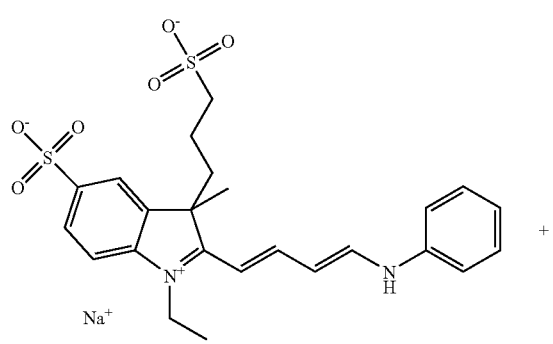

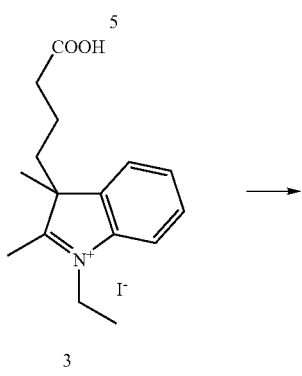

516 mg (1 mmol) 1-ethyl-3-methyl-2-((1E,3E)-4-phenylamino-buta-1,3-dienyl)-5-sulfo-3-(3-sulfo-propyl)-3H-indolium sodium salt 5 and 387 mg (1 mmol) 3-(3-carboxypropyl)-2,3-dimethyl-1-ethyl-3H-indolium iodide salt 3 were dissolved in a mixture of 10 ml acetic acid and 10 ml acetic anhydride. Subsequently, 5 ml pyridine was added. The solution was stirred under reflux for 15 minutes. After cooling to room temperature (about 20° C. to about 22° C.), 20 ml ether was added. The precipitate that was obtained was extracted by suction, washed with ether and dried.

The residue was purified by column chromatography: RP-18: methanol/water 1/1.

After cooling to room temperature (about 20° C. to about 22° C.), 20 ml ether was added. The precipitate that was obtained, which was a mixture of the diastereomers 6.1 and 6.2, was extracted by suction, washed with ether, and dried.

The residue was purified by column chromatography: RP-18: methanol/water 1/1.

The fractions containing the pure compounds 6.1 were combined and the solvent was removed by distillation. Similarly, the fractions containing pure compound 6.2 were combined and evaporated. The yield was about 15% per diastereomer.

Diastereomer 6.1:

UV-vis (ethanol): $\lambda_{max}$=650 nm

MS (ESI–): 766.2 [M]$^-$

Diastereomer 6.2:

UV-vis (ethanol): $\lambda_{max}$=647 nm

MS (ESI–): 766.1 [M]$^-$

EXAMPLE 3

General Synthesis of N-Hydroxysuccinimidyl Esters ($X_1$=—NHS)

Pure diasteromeric compound of type Ia, Ib, IIa, or IIb with $X_1$=OH (20 µmol), 8 mg (40 µmol) dicyclohexylcarbodiimide, and 5 mg (40 µmol) N-hydroxysuccinimide were dissolved in 2 ml DMF and 100 µl water. Six µl (40 µmol) triethylamine was added. The reaction mixture was stirred at room temperature (about 20° C. to about 22° C.) for 24 hours and then filtered. The solvent was removed and the residue was washed with diethylether. The reaction proceeded quantitatively.

EXAMPLE 4

General Synthesis of Maleimides ($X_1$=—NH—$CH_2CH_2$-Maleimide)

N-hydroxysuccinimide-ester of the pure diastereomeric compound of type Ia, Ib, IIa, or IIb with $X_1$=NHS (20 µmol) is dissolved in 2 ml DMF and 100 µl water and mixed with 7.6 mg (30 µmol) 2-maleimidoethylamine-trifluoracetate and 5 µl (30 µmol) N-ethyldiisopropyl-amine. The reaction mixture is stirred for three hours at room temperature (about 20° C. to about 22° C.). The solvent is evaporated under reduced pressure. The residue is washed with diethylether and acetone and dried in a vacuum. The reaction proceeds quantitatively.

EXAMPLE 5

General Synthesis of Iodoacetamides ($X_1$=—NH—$CH_2CH_2$—NH—CO—$CH_2$—I)

N-hydroxysuccinimide-ester of the pure diastereomeric compound of type Ia, Ib, IIa, or IIb with $X_1$=NHS (20 µmol) is dissolved in 2 ml DMF and 100 µl water, followed by addition of 40 mg (300 µmol) ethylendiamine dihydrochloride and 26 µl (150 µmol) N-ethyldiisopropylamine. The reaction mixture is stirred for three hours at room temperature (about 20° C. to about 22° C.). The solvent is then evaporated under reduced pressure, the residue is dissolved in methanol, and the ethylendiamine dihydrochloride removed by filtration. The methanol is evaporated under reduced pressure.

The residue is dissolved in 2 ml dry DMF, followed by the addition of 7 mg (25 µmol) N-succinimidyl iodoacetate and 4 µl (25 µmol) N-ethyldiisopropylamine. The reaction mixture is stirred for three hours at room temperature. The solvent is evaporated under reduced pressure and the residue purified by reverse phase HPLC.

EXAMPLE 6

Conjugation to Deoxyribonucleic Acid (DNA)

Dye NHS esters were conjugated to dNTPs using the following general conditions.

A stock solution of acaa-dUTP or acaa-dCTP (2 mM) was made in 0.1 M sodium borate buffer (pH 9). The dye NHS ester (1 mg) was dissolved in 40 µl anhydrous DMSO and mixed with 500 µl of the nucleotide stock solution. The reaction mixture was agitated at room temperature (about 20° C. to about 22° C.) for about 4 to 6 hours in the dark. The reaction mixture was loaded on a Zorbax oligo column (Agilent, 5 µm, 9.4×250 mm). The column was washed with 20% $CH_3CN$ in 20 mM sodium phosphate buffer and eluted with a gradient of 1M NaCl in 20% $CH_3CN$ and 20 mM sodium phosphate. The target fraction was collected and concentrated. The residue was dissolved in 50 mM LiCl and loaded onto 1 ml C18 sample preparation cartridge. The cartridge was washed with 1 ml $H_2O$. The product was eluted with 2 ml $H_2O$ and 2 ml $CH_3CN/H_2O$ (v/v=1/1). The collected product was concentrated down and formulated to 1 mM concentration in 10 mM sodium phosphate buffer (pH 7).

Compound formula IIb conjugated to dUTP, as shown below,

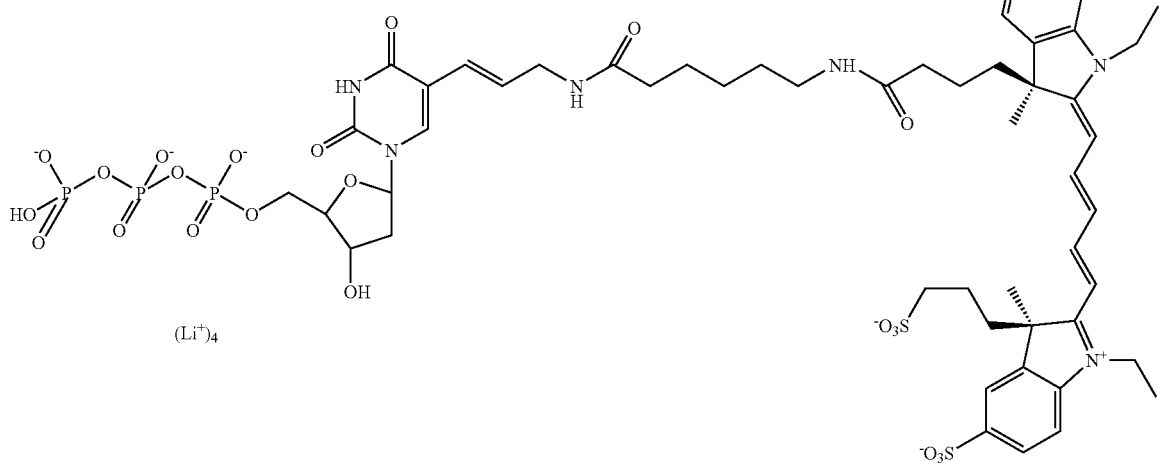

was mixed with 0.2 mM of each of the triphosphates of dA, dC, and dG and 0.16 mM unlabeled dUTP, Taq polymerase (0.1 unit per µL of reaction mix) and template DNA in buffer (10 mM Tris, pH 9.0, 50 mM KCl, and 1.5 mM $MgCl_2$). The enzyme incorporated some of the labeled dUTP and the product was detected by fluorescence.

The reaction was repeated with each of compounds formulas Ia, IIb2, IIb1, (IIb2 and IIb1 are diastereoisomers). The amount of fluorescence varied depending upon the amount of the labeled dUTP incorporated.

A Taq polymerase primer extension assay was performed in conjugates of dUTP including compound formulas IIa and IIb. The results demonstrated improvement in relative fluorescence units (RFU) using compound formulas IIa and IIb. Between two of the diastereomers of compound IIb, diastereomer 1 (IIb-1) demonstrated 35% higher RFU than diastereomer 2 (IIb-2) (53 RFU and 64.4 RFU versus 21 RFU respectively. The relative fluorescence among the compounds was IIb-1 (87 RFU)>IIb-2 (64.4, 53 RFU)>Ia (21 RFU).

The diastereomers can be separated, have different chemical properties, and may have different affinities for DNA polymerases. The difference in RFU between these two diastereomers may be indicative of a structural preference by Taq polymerase for one of the isomers.

EXAMPLE 7

Conjugation to Ribonucleic Acid (RNA)

Dye NHS esters are conjugated to NTPs using the following general conditions:

A stock solution of acaa-UTP (2 mM) is made in 0.1 M sodium borate buffer (pH 9). The dye NHS ester (1 mg) is dissolved in 40 μl anhydrous DMSO and mixed with 500 μl of the nucleotide stock solution. The reaction mixture is agitated at room temperature (about 20° C. to about 22° C.) for about 4 to 6 hours in the dark. The reaction mixture is loaded on a Zorbax oligo column (Agilent, 5 μm, 9.4×250 mm). The column is washed with 20% $CH_3CN$ in 20 mM sodium phosphate buffer and eluted with a gradient of 1M NaCl in 20% $CH_3CN$ and 20 mM sodium phosphate. The target fraction is collected and concentrated. The residue is dissolved in 50 mM LiCl and loaded onto a 1 ml C18 sample preparation cartridge. The cartridge is washed with 1 ml $H_2O$. The product is eluted with 2 ml $H_2O$ and 2 ml $CH_3CN/H_2O$ (v/v=1/1). The collected product is concentrated down and formulated to 1 mM concentration in 10 mM sodium phosphate buffer (pH 7).

Compound IIb, conjugated to UTP, as shown below

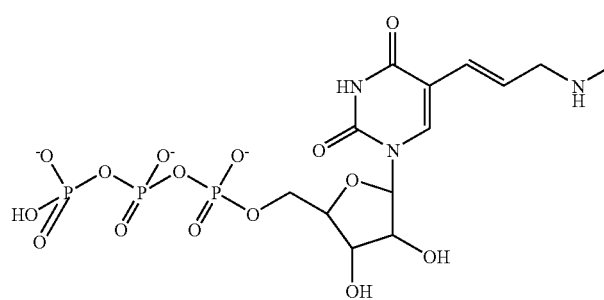
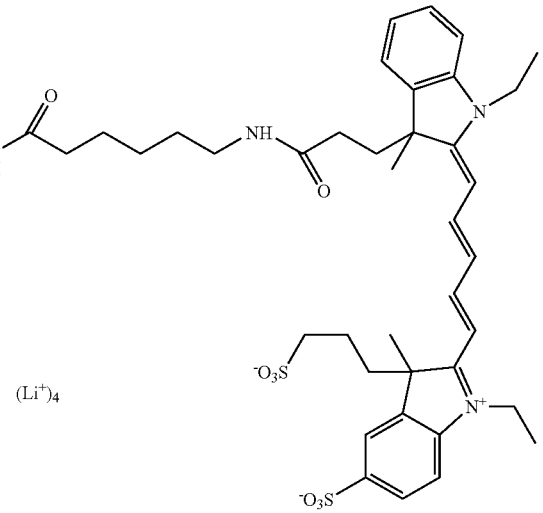

is used to synthesize labeled RNA from T-7 RNA polymerase and a T-7 RNA polymerase promoter containing-template in the presence of a mixture of ribonucleotides (ATP, GTP, CTP and UTP) and varying amounts of labeled UTP (0-50%) in a buffer containing 4 mM Tris HCl, 2.5 mM NaCl, 0.2 mM spermidine, 1 mM DTT, 2.4 mM $MgCl_2$ and inorganic pyrophosphate. RNA synthesis reactions are carried out at 37° C. for 2 hours and the labeled RNA synthesized is purified using a gel filtration column such as Sephadex G-25.

EXAMPLE 8

Fluorescence In-Situ Hybridization (FISH)

For cells with visible cytoplasm surrounding interphase and metaphase, slides are prepared by incubating the cells in 0.01 M HCl with 0.005% pepsin at 37° C. for ten minutes. The slides are then washed 2×1 minutes in PBS and incubated for ten minutes in 1% formaldehyde in PBS. The slides are incubated for 2×1 minute in PBS and then dehydrated in 70% ethanol for one minute, then at 95% ethanol for one minute, then at 100% ethanol for one minute, before air drying.

Ten μl of compounds of formulas I or II (e.g., compound formulas Ia, Ib, IIa, IIb) labeled probe for each target is dispensed into a 0.5 ml microcentrifuge tube and then incubated at 96° C. for five minutes in a water bath. The tubes are briefly centrifuged, then 10 μl of the probe mix is applied to each target and covered with a coverslip. The slides and probes are denatured for two minutes at 80° C. on a temperature controlled hot plate and then incubated for 12-18 h in a humidified environment at 37° C.

The cover slip is removed by soaking in 2×SSC/0.1% Tween-20 at 37° C. The slide is then washed 4×5 min in 0.5×SSC/0.1% SDS at 60° C. to 65° C., and then briefly rinsed with distilled water and air dried out of direct light. DAPI anti-fade solution (20 μl) is applied to the target and covered with a cover slip (24 mm×50 mm) before viewing on a fluorescent microscope. Fluorescence will be detected when hydridization occurs.

EXAMPLE 9

Microarrays

Microarray analysis of Interleukin (IL)-2, IL-8, IL-12p70, and tumor necrosis factor (TNF)α is performed using human Inflammation I Array (Pierce Biotechnology, Inc.) with standards supplied. Rabbit antibodies for IL-2 and IL-8, and biotinylated mouse antibodies for IL-12p70 and TNFα are diluted to 1 μg/ml in 1% BSA/dPBS and then used as detection antibodies. Compounds of formula I or II conjugates of goat anti-rabbit (GAR), streptavidin (SA), and NeutrAvidin® (NA) are diluted to 0.1 μg/ml and then used for fluorescent detection of the probes.

Glass slides containing a microarray of human inflammatory proteins are equilibrated to room temperature in a desiccator. The slides are blocked for fifteen min using 1% bovine serum albumin (BSA)/5% sucrose/Dulbecco's phosphate buffered saline (DPBS) in screw cap slide holders and then dried in a slide centrifuge for thirty sec. Slide overlays are placed on the blocked slides and rinsed once with PBS containing 0.05% Tween-20 (PBST).

The antigen set is applied for two hours at 50 μl of a 1000 μg/ml stock solution per subarray. The slides are rinsed three times with PBST. Rabbit antibodies for IL-2 and IL-8, and biotinylated mouse antibodies for IL-12p70 and TNFalpha are applied for one hour at 50 μl of a 1 μg/ml stock solution. The slide is rinsed three times with PBST. The pure diastereomeric compounds of formula I or II conjugates of goat anti-rabbit, SA, and NA are applied for one hour at 50 μl of a 0.1 μg/ml stock solution. The slides are washed five times with PBST, removed from the frame, and dipped in 0.25×PBS for 5 sec, and then dried by centrifugation for about 30 sec.

EXAMPLE 10

Flow Cytometry

Flow cytometry is used to evaluate CD3 receptor on Jurkat cells with a compounds of formula I or II labeled goat anti-mouse secondary antibody.

Jurkat cells are centrifuged for five minutes at 4000 rpm, washed with 1×3 ml dPBS, and resuspended in 5 ml dPBS. Cell concentration is adjusted to 28×10$^6$ cells/ml. Cells are incubated for 45 min in mouse anti-CD3 antibody (0.625 μg/ml), centrifuged for five min and washed with 2×1 ml PBS. Cells are incubated for 45 min in compounds of formula I or II labeled goat anti-mouse diluted in dPBS (2.7 μg/ml).

Cells are then centrifuged as previously described, washed 2×1 ml in dPBS, and resuspended in 300 μl dPBS. Data are collected on a Becton Dickinson FACSCalibur® flow cytometer with four color fluorescence capability.

EXAMPLE 11

High Throughput Screening

Functional assays are performed on serially diluted 96-well white opaque biotinylated-BSA coated plates (2 μg/ml to 0 μg/ml). Plates are washed three times with 200 μl PBS containing 0.05% Tween and one time with 200 μl PBS. Compounds of formula I or II streptavidin (SA) and Alexa® 647 (Invitrogen, Carlsbad Calif.)-SA conjugates are diluted 0.004 mg/ml in PBS. Diluted conjugates are applied to the wells of the plates (100 μl/well). Plates, covered and protected from light, are incubated for one hour and then washed as in Example 10. PBS is added to the plates (100 μl/well) and the fluorescent intensity is captured using the Tecan Safire at Cy5 setting.

EXAMPLE 12

Use of Diastereomers as Labels

Ten mg streptavidin (SA) at 10 mg/ml is reconstituted in 50 mM borate buffer, pH 8.4. SA is labeled with a 5 molar excess of the pure diastereomeric compounds of formula I or II with $X_1$=—NHS that is reconstituted in 0.1 ml MilliQ water. The reaction is carried out for two hours at room temperature. The excess unreacted compound is removed by dialyzing the sample overnight against 3×5 L of 0.1 M sodium phosphate buffer, 0.15 M NaCl, pH 7.2 (PBS). Three changes of PBS are used.

Ten mg streptavidin at 10 mg/ml is reconstituted in 50 mM borate buffer, pH 8.4. SA is labeled with a 4 molar excess of the pure diastereomeric compounds of formula I or II with $X_1$=—NHS that is reconstituted in 0.1 ml MilliQ water. The reaction is carried out for two hours at room temperature. The excess unreacted dye is removed by dialyzing the sample overnight against 3×5 L of 0.1 M sodium phosphate buffer, 0.15 M NaCl, pH 7.2 (PBS). Three changes of PBS are used.

EXAMPLE 13

PCR Reactions Using Taq DNA Polymerase

Compounds 4 (p. 15) and 6 (p. 16) were evaluated in PCR reaction. The amplicon is 378-bp fragment of human GAPD (H) gene (SEQ ID NO:1). The GAPD(H) forward primer sequence is 5'-CCA CCC AGA AGA CTG TGG AT-3' (SEQ ID NO:2). The GAPD(H) Reverse primer sequence is 5'-TGA CAA AGT GGT CGT TGA GG-3' (SEQ ID NO:3). The PCR reactions were prepared as shown in Table 1.

TABLE 1

| Reagent | Volume | Final |
| --- | --- | --- |
| 10X PCR buffer | 2 μl | 1x |
| 25 mM MgCl$_2$ | 2 μl | 2.5 mM |
| 1 mM dVTP Mixture | 1 μl | 0.05 mM |
| 1 mM dye-dUTP/dTTP Mixture | 1 μl | 0.05 mM |
| GAPDH Fwd primer | | 0.5 μM |
| GAPDH Rev primer | | 0.5 μM |
| 2 ng/μl DNA template | 0.4 μl | 0.8 ng |
| 5 unit/μl Taq DNA polymerase | 0.08 μl | 0.02 |

Add autoclaved ddH$_2$O to 20 μl final reaction volume

The PCR reaction mixture was subjected to the PCR thermal cyclic steps of initial denature at 95° C. for two minutes, then 30 cycles of 95° C. for 30 seconds, 55° C. for 30 seconds and 72° C. for one minute. PCR products were resolved in 2% agarose gel and visualized by CCD camera. The PCR yield, shown in Table 2, was determined by comparing the band density of ethidium bromide stained gels.

TABLE 2

| % of dye-dUTP | 0 | 5 | 10 | 15 | 25 | 35 | 50 |
| --- | --- | --- | --- | --- | --- | --- | --- |
| compound 4.1 - dUTP | 100% | 88% | 74% | 82% | 79% | 68% | 42% |
| compound 4.2 - dUTP | 100% | 81% | 81% | 78% | 57% | 49% | 14% |
| compound 6.1 - dUTP | 100% | 98% | 87% | 73% | 53% | 35% | 15% |
| compound 6.2 - dUTP | 100% | 97% | 83% | 66% | 47% | 35% | 19% |

The relative fluorescent intensity, shown in Table 3, was calculated using the fluorescent intensity of the amplicon band.

TABLE 3

| % of dye-dUTP | 0 | 5 | 10 | 15 | 25 | 35 | 50 |
| --- | --- | --- | --- | --- | --- | --- | --- |
| compound 4.1 - dUTP | 0% | 6% | 16% | 34% | 60% | 78% | 100% |
| compound 4.2 - dUTP | 0% | 18% | 40% | 59% | 63% | 100% | 26% |
| compound 6.1 - dUTP | 0% | 29% | 49% | 65% | 100% | 82% | 54% |
| compound 6.2 - dUTP | 0% | 23% | 38% | 55% | 71% | 83% | 100% |

Figure 2:
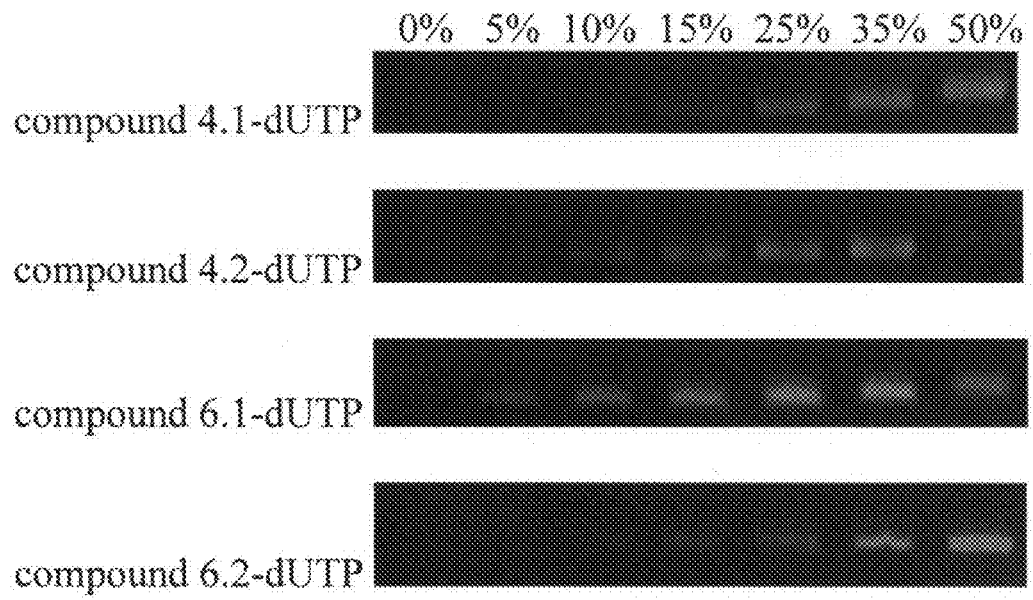
FIG. 2 shows fluorescent images of PCR products amplified in the presence of a deoxynucleotide triphosphate labeled with a disclosed compound.

FIG. 1 shows ethidium bromide stained gels of PCR products amplified in the presence of 0% to 50% compound 4-dUTP and compound 6-dUTP. FIG. 2 shows fluorescent images of PCR products amplified in the presence of 0% to 50% compound 4-dUTP and compound 6-dUTP.

EXAMPLE 14

PCR Reactions Using Different DNA Polymerases

The incorporation of compound 4-dUTP and compound 6-dUTP in PCR reactions was evaluated using different DNA polymerases. The PCR reactions were prepared as shown in Table 4.

TABLE 4

| Stock | | Final | | | | |
|---|---|---|---|---|---|---|
| DNA polymerase | Taq | Vent exo- | Deep Vent exo- | Tth | KOD | Pfu |
| DNA Polymerase | 0.02 u/μl | 0.04 u/μl | 0.04 u/μl | 0.02 u/μl | 0.02 u/μl | 0.05 u/μl |
| 10X PCR buffer for each enzyme | 1x | 1x | 1x | 1x | 1x | 1x |
| 25 mM MgCl$_2$ | 2.5 mM | | | | 1.5 mM | |
| 1 mM dVTP Mixture | 0.05 mM | 0.05 mM | 0.05 mM | 0.05 mM | 0.05 mM | 0.05 mM |
| 35% 1 mM dye-dUTP/dTTP Mixture | 0.05 mM | 0.05 mM | 0.05 mM | 0.05 mM | 0.05 mM | 0.05 mM |
| GAPDH Fwd primer | 0.5 μM | 0.5 μM | 0.5 μM | 0.5 μM | 0.5 μM | 0.5 μM |
| GAPDH Rev primer | 0.5 μM | 0.5 μM | 0.5 μM | 0.5 μM | 0.5 μM | 0.5 μM |
| 2 ng/μl DNA template | 0.8 ng | 0.8 ng | 0.8 ng | 0.8 ng | 0.8 ng | 0.8 ng |

Add autoclaved ddH$_2$O to 20 μl final reaction volume

A mixture of 35% compound 4-dUTP or 35% compound 6-dUTP in dTTP was used in the reaction. The target amplicon, the primers and the PCR cycle conditions were the same as those described in Example 13. Vent (exo−), Deep Vent (exo−), Tth, KOD, and Pfu DNA polymerases were used. The PCR yields are shown in Table 5.

TABLE 5

| | Taq | Vent exo- | Deep Vent exo- | Tth | KOD | Pfu |
|---|---|---|---|---|---|---|
| compound 4.1 - dUTP | 100% | 60% | 86% | 45% | 43% | 93% |
| compound 4.2 - dUTP | 100% | — | 88% | 85% | 38% | 35% |
| compound 6.1 - dUTP | 100% | 9% | 11% | 149% | 12% | 10% |
| compound 6.2 - dUTP | 100% | 27% | 25% | 85% | 9% | 22% |

The relative fluorescent intensities of PCR Reactions Using Different DNA Polymerases are shown in Table 6.

TABLE 6

| | Taq | Vent exo- | Deep Vent exo- | Tth | KOD | Pfu |
|---|---|---|---|---|---|---|
| compound 4.1 - dUTP | 100% | 204% | 385% | 19% | 54% | 185% |
| compound 4.2 - dUTP | 100% | — | 400% | 40% | 80% | 76% |
| compound 6.1 - dUTP | 100% | 0% | 26% | 156% | 28% | 0% |
| compound 6.2 - dUTP | 100% | 149% | 169% | 81% | 5% | 217% |

Figure 3:
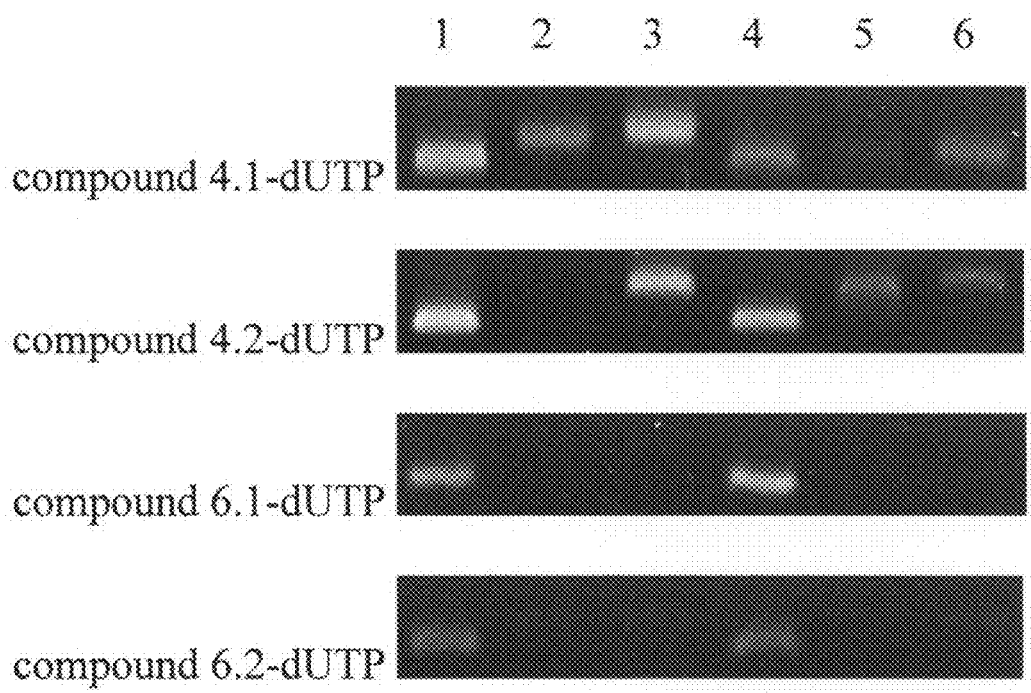
FIG. 3 shows ethidium bromide stained gels of PCR products amplified in the presence of a deoxynucleotide triphosphate labeled with a disclosed compound.
Figure 4:
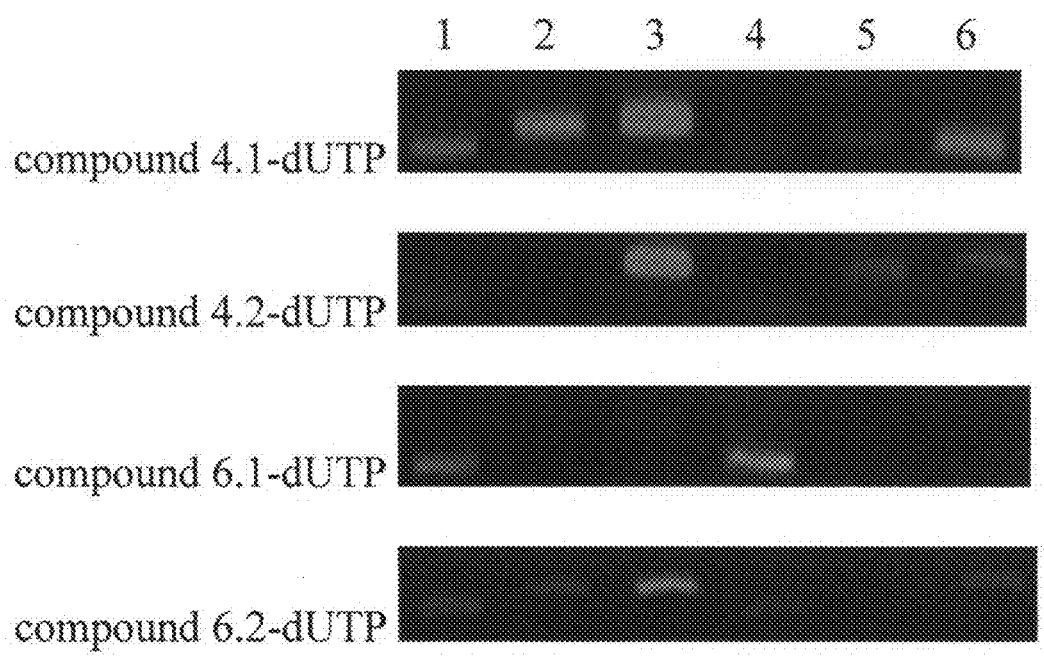
FIG. 4 shows fluorescent images of PCR products amplified in the presence of a deoxynucleotide triphosphate labeled with a disclosed compound.

FIG. 3 shows ethidium bromide stained gels of PCR products amplified in the presence of 35% compound 4-dUTP or compound 6-dUTP in the mixture with dTTP and different DNA polymerases. Lane 1 Taq DNA polymerase, Lane 2 Vent (exo−) DNA polymerase, Lane 3 Deep Vent (exo−) DNA polymerase, Lane 4 Tth DNA polymerase, Lane 5 KOD DNA polymerase, Lane 6 Pfu DNA polymerase. FIG. 4 shows fluorescent images of PCR products amplified in the presence of 35% compound 4-dUTP or compound 6-dUTP in the mixture with dTTP and different DNA polymerases. Lane 1 Taq DNA polymerase, Lane 2 Vent (exo−) DNA polymerase, Lane 3 Deep Vent (exo−) DNA polymerase, Lane 4 Tth DNA polymerase, Lane 5 KOD DNA polymerase, Lane 6 Pfu DNA polymerase.

In one embodiment, a kit contains at least one of the compounds of formulas I or II and instructions for using the compounds in labeling a biomolecule. In one embodiment, a kit contains at least one biomolecule labeled with at least one of the compounds of formulas I or II and instructions for using the labeled biomolecule. The biomolecule may be a nucleoside triphosphate or a deoxynucleoside triphosphate. The use may be a polymerase reaction.

Applicants incorporate by reference the material contained in the accompanying computer readable Sequence Listing identified as SEQ_ST25.txt, having a file creation date of Sep. 11, 2009 1:46:28 P.M. and file size of 1.3 kilobytes.

It should be understood that the embodiments and examples described are only illustrative and are not limiting in any way. For example, any of the compounds may be used in the above examples. Therefore, various changes, modifications or alterations to these embodiments may be made or resorted to without departing from the spirit of the invention and the scope of the following claims.

What is claimed is:

1. At least one of a diastereomeric compound of the general formula I or formula II wherein formula I compounds are Ia1, Ia2, Ia3 and Ia4 and formula II compounds are IIa1, IIa2, IIa3 and IIa4

I

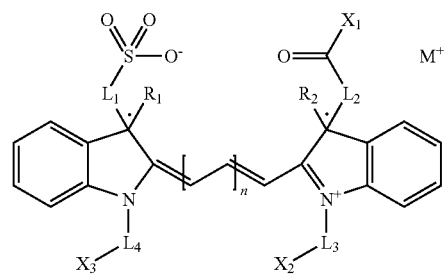

Ia1

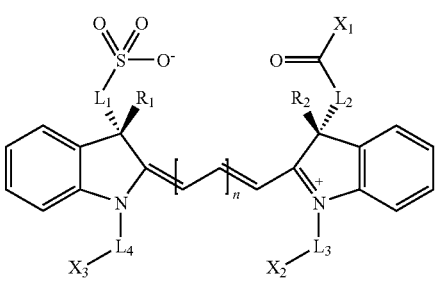

Ia2

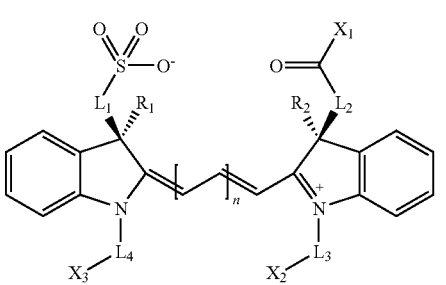

Ia3

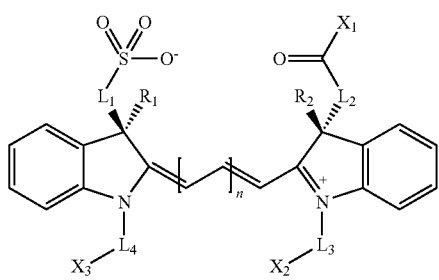

Ia4

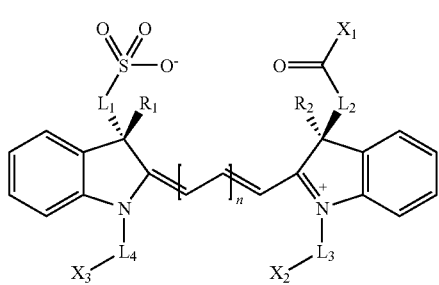

II

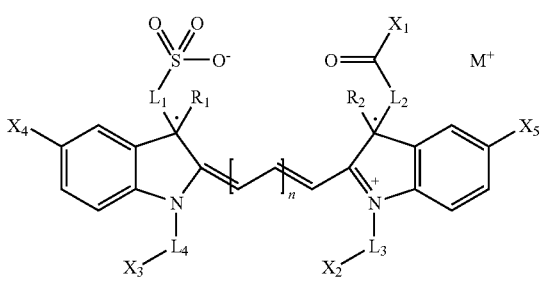

-continued

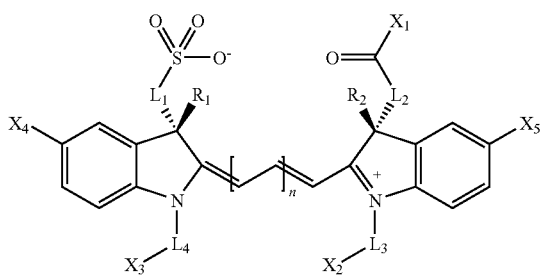

IIa1

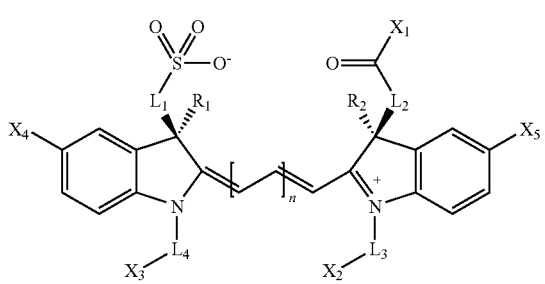

IIa2

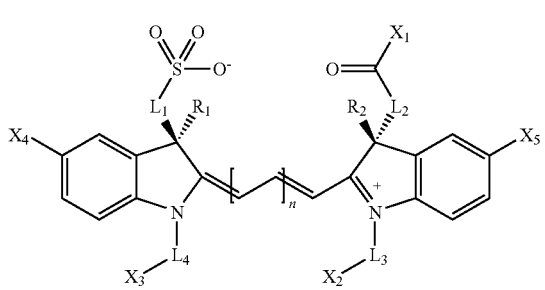

IIa3

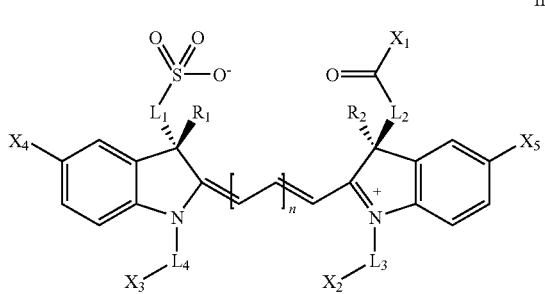

IIa4 wherein
each of $R_1$ and $R_2$ is the same or different and is independently selected from the group consisting of an aliphatic and heteroaliphatic group;
each of $L_1$ to $L_4$ is the same or different and is independently selected from the group consisting of a divalent linear (—$(CH_2)_o$—, o=1 to 15), crossed, or cyclic alkylene group which can be substituted by at least one atom selected from the group consisting of oxygen, substituted nitrogen, and sulfur;
$X_1$ is selected from the group consisting of —OH, —SH, —$NH_2$, —NH—$NH_2$, —F, —Cl, —Br, —I, —NHS (hydroxysuccinimidyl/sulfosuccinimidyl), —O-STP (4-sulfo-2,3,5,6-tetrafluorophenoxy), —O-TFP (2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2H$, —NR-L-$CO_2$—NHS, —NR-L-$CO_2$-STP, —NR-L-$CO_2$-TFP, —NR-L-CO-benzotriazole, —NR-L-CHO, —NR-L-maleimide, and —NR-L-NH—CO—$CH_2$—I;

R is —H or is equal to $R_1$ or $R_2$;
L is equal to $L_1$ to $L_4$;
each of $X_2$ and $X_3$ is the same or different and is independently selected from the group consisting of hydrogen, alkyl-, tert-alkyl-, aryl-, carboxyaryl-, dicarboxyaryl-, heteroaryl-, cycloalkyl-, heterocycloalkyl-, alkyloxy-, alkylmercapto-, aryloxy, arylmercapto, hydroxy-, amino-, nitro-, and cyano-residues, or is a solubilizing or ionizable substituent selected from the group consisting of —$SO_3^-$, —$PO_3^{2-}$, —$CO_2^-$, tert-ammonium, cyclodextrine, sugar, and combinations thereof; with the proviso that in Formula I, one of $X_2$ or $X_3$ is —$SO_3^-$;
in Formula II, one of $X_4$ or $X_5$ is hydrogen and the other is —$SO_3^-$;
$M^+$ is a number of $Na^+$, $K^+$, $Ca^{2+}$, ammonia, or other cation(s) needed to compensate the negative charge brought by the cyanine; and
n is an integer from 1 to 3.

2. The compound of claim 1 wherein
each of $R_1$ and $R_2$ is a C1-C3 alkyl group;
each of $L_1$ and $L_2$ is a C3-C5 alkylene group;
$X_1$ is OH or —NHS;
each of $L_3$ and $L_4$ is a C1-C3 alkylene group;
each of $X_2$ or $X_3$ is a C1-C3 alkyl or —$SO_3^-$; and
n is 2.

3. The compound of claim 1 wherein
each of $R_1$ and $R_2$ is methyl;
each of $L_1$ and $L_2$ is propylene;
$X_1$ is OH;
one of $L_3$ or $L_4$ is methylene and the other is propylene;
one of $X_2$ or $X_3$ is methyl and the other is —$SO_3^-$; and
n is 2.

4. The compound of claim 1 wherein
each of $R_1$ and $R_2$ is a C1-C3 alkyl group;
each of $L_1$ and $L_2$ is a C3-C5 alkylene group;
$X_1$ is OH or —NHS;
each of $L_3$ and $L_4$ is a C1-C3 alkylene group;
each of $X_2$ or $X_3$ is a C1-C3 alkyl;
one of $X_4$ or $X_5$ is H and the other is —$SO_3^-$; and
n is 2.

5. The compound of claim 1 wherein
each of $R_1$ and $R_2$ is methyl;
each of $L_1$ and $L_2$ is propylene;
$X_1$ is OH;
each of $L_3$ and $L_4$ is methylene;
each of $X_2$ or $X_3$ is methyl;
one of $X_4$ or $X_5$ is H and the other is —$SO_3^-$; and
n is 2.

6. The compound of claim 1 of general formula I, wherein the compound is

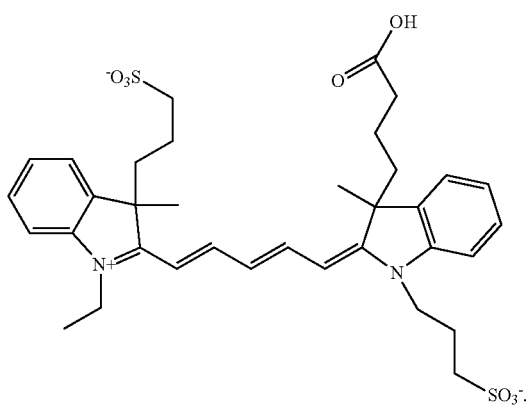

7. The compound of claim 1 of general formula I, wherein the compound is

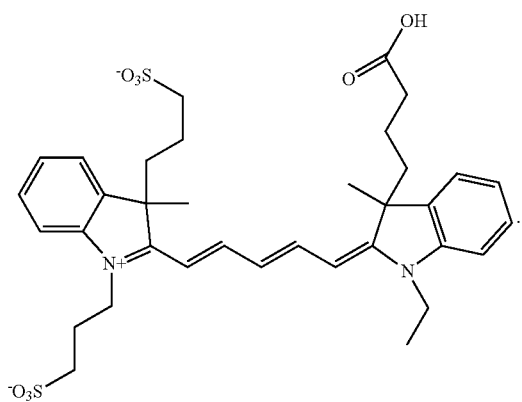

8. The compound of claim 1 of general formula II, wherein the compound is

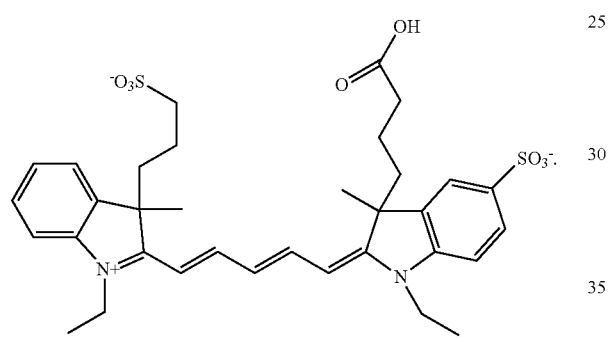

9. The compound of claim 1 of general formula II, wherein the compound is

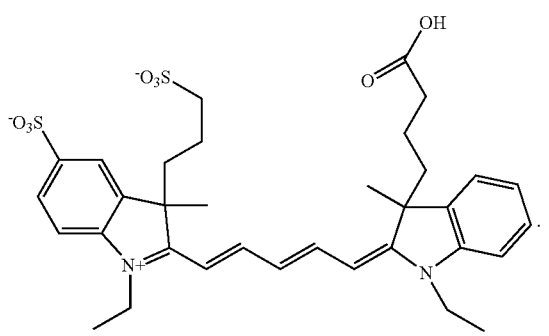

10. The compound of claim 1 conjugated to a biomolecule selected from the group consisting of a protein, antibody, enzyme, deoxyribonucleoside triphosphate (dNTP), ribonucleoside triphosphate (NTP), oligonucleotide, biotin, hapten, cofactor, lectin, antibody binding protein, carotenoid, hormone, neurotransmitter, growth factors, toxin, biological cell, lipid, receptor binding drug, organic polymer carrier material, inorganic polymeric carrier material, and combinations thereof.

11. A biocompatible dye composition comprising at least one biocompatible excipient and a compound of at least one of a diastereomeric compound of the general formula I or formula II wherein formula I compounds are Ia1, Ia2, Ia3 and Ia4 and formula II compounds are IIa1, IIa2, IIa3 and IIa4

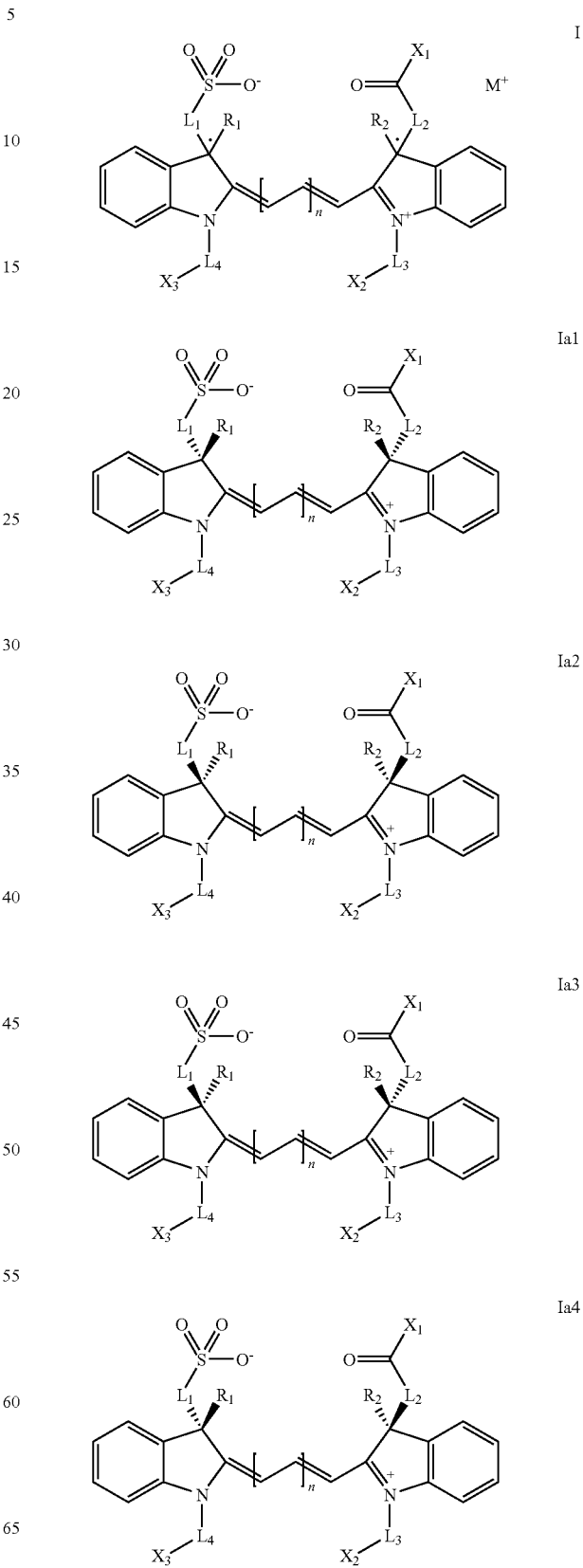

-continued

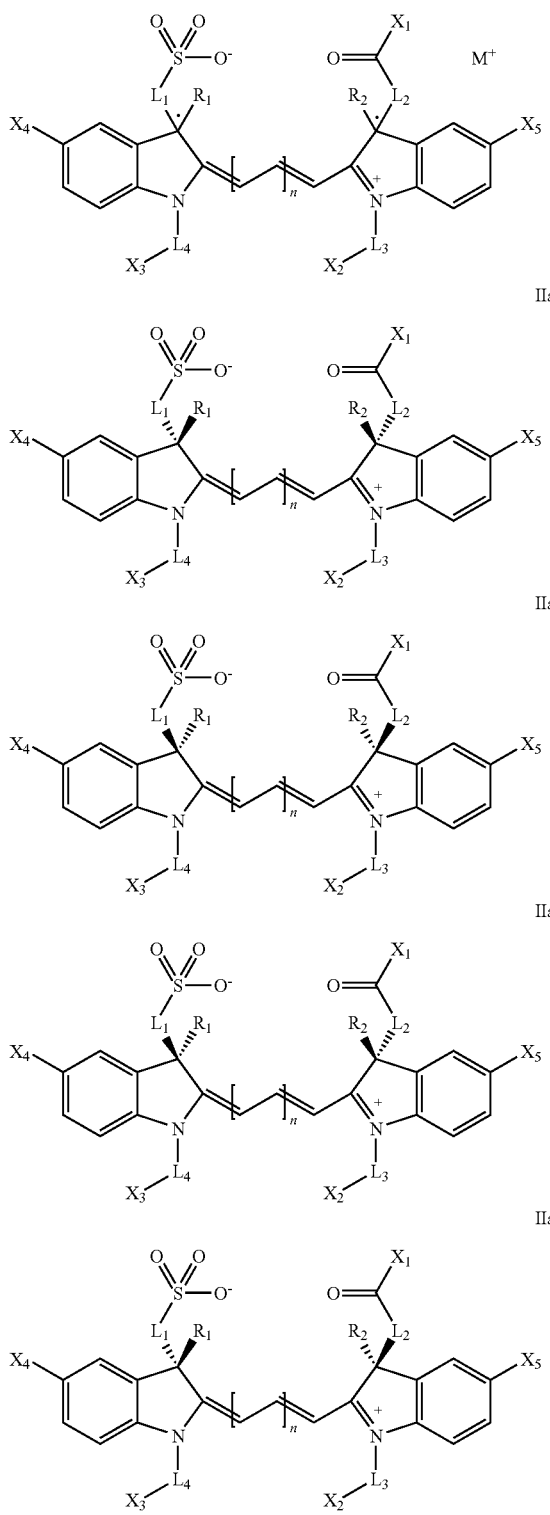

II

IIa1

IIa2

IIa3

IIa4 wherein
each of $R_1$ and $R_2$ is the same or different and is independently selected from the group consisting of an aliphatic and heteroaliphatic group;
each of $L_1$ to $L_4$ is the same or different and is independently selected from the group consisting of a divalent linear (—$(CH_2)_o$—, o=1 to 15), crossed, or cyclic alkylene group which can be substituted by at least one atom selected from the group consisting of oxygen, substituted nitrogen, and sulfur;
$X_1$ is selected from the group consisting of —OH, —SH, —$NH_2$, —NH—$NH_2$, —F, —Cl, —Br, —I, —NHS (hydroxysuccinimidyl/sulfosuccinimidyl), —O-STP (4-sulfo-2,3,5,6-tetrafluorophenoxy), —O-TFP (2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-$CO_2$—NHS, —NR-L-$CO_2$-STP, —NR-L-$CO_2$-TFP, —NR-L-CO-benzotriazole, —NR-L-CHO, —NR-L-maleimide, and —NR-L-NH—CO—$CH_2$—I;
R is —H or is equal to $R_1$ and $R_2$;
L is equal to $L_1$ to $L_4$;
each of $X_2$ and $X_3$ is the same or different and is independently selected from the group consisting of hydrogen, alkyl-, tert-alkyl-, aryl-, carboxyaryl-, dicarboxyaryl-, heteroaryl-, cycloalkyl-, heterocycloalkyl-, alkyloxy-, alkylmercapto-, aryloxy, arylmercapto, hydroxy-, amino-, nitro-, and cyano-residues, or is a solubilizing or ionizable substituent selected from the group consisting of —$SO_3^-$, —$PO_3^{2-}$, —$CO_2^-$, tert-ammonium, cyclodextrine, sugar, and combinations thereof; with the proviso that in Formula I, one of $X_2$ or $X_3$ is —$SO_3^-$;
in Formula II one of $X_4$ or $X_5$ is hydrogen and the other is —$SO_3^-$;
$M^+$ is number of $Na^+$, $K^+$, $Ca^{2+}$, ammonia, or other cation(s) needed to compensate the negative charge brought by the cyanine; and
n in formula I is a integer from 1-3.

12. The composition of claim 11 wherein the compound is conjugated to a biomolecule selected from the group consisting of a protein, antibody, enzyme, deoxyribonucleotide triphosphate (dNTP), ribonucleotide triphosphate (NTP), oligonucleotide, biotin, hapten, cofactor, lectin, antibody binding protein, carotenoid, hormone, neurotransmitter, growth factors, toxin, biological cell, lipid, receptor binding drug, organic polymeric carrier material, inorganic polymeric carrier material, and combinations thereof.

13. A kit comprising at least one of the compounds of claim 1, and instructions for labeling a biomolecule with the compound.

14. A kit comprising at least one compound-labeled biomolecule wherein the compound is described in claim 1, and instructions for using the compound-labeled biomolecule in a polymerase reaction, wherein the compound-conjugated biomolecule comprises at least one of the compounds of claim 1 and at least one of a nucleoside triphosphate or a deoxynucleoside triphosphate.

* * * * *

SEQUENCE LISTING

<160> NUMBER OF SEQ ID NOS: 3

<210> SEQ ID NO 1
<211> LENGTH: 378
<212> TYPE: DNA
<213> ORGANISM: Homo sapiens

<400> SEQUENCE: 1

```
ccacccagaa gactgtggat ggcccctccg ggaaactgtg gcgtgatggc cgcggggctc      60
tccagaacat catccctgcc tctactggcg ctgccaaggc tgtgggcaag gtcatccctg     120
agctgaacgg gaagctcact ggcatggcct tccgtgtccc cactgccaac gtgtcagtgg     180
tggacctgac ctgccgtcta gaaaaacctg ccaaatatga tgacatcaag aaggtggtga     240
agcaggcgtc ggagggcccc ctcaagggca tcctgggcta cactgagcac caggtggtct     300
```

```
cctctgactt caacagcgac acccactcct ccacctttga cgctggggct ggcattgccc    360
tcaacgacca ctttgtca                                                  378

<210> SEQ ID NO 2
<211> LENGTH: 20
<212> TYPE: DNA
<213> ORGANISM: Artificial Sequence
<220> FEATURE:
<223> OTHER INFORMATION: Primer sequence

<400> SEQUENCE: 2
ccacccagaa gactgtggat                                                20

<210> SEQ ID NO 3
<211> LENGTH: 20
<212> TYPE: DNA
<213> ORGANISM: Artificial Sequence
<220> FEATURE:
<223> OTHER INFORMATION: Primer sequence

<400> SEQUENCE: 3
tgacaaagtg gtcgttgagg                                                20
```